US010219700B1

(12) United States Patent
Yang et al.

(10) Patent No.: US 10,219,700 B1
(45) Date of Patent: Mar. 5, 2019

(54) SYSTEMS AND METHODS FOR QUASI-BALLISTIC PHOTON OPTICAL COHERENCE TOMOGRAPHY IN DIFFUSIVE SCATTERING MEDIA USING A LOCK-IN CAMERA DETECTOR

(71) Applicant: HI LLC, Los Angeles, CA (US)

(72) Inventors: Changhuei Yang, South Pasadena, CA (US); Adam Marblestone, Arlington, MA (US); Jamu Alford, Simi Valley, CA (US)

(73) Assignee: HI LLC, Los Angeles, CA (US)

( * ) Notice: Subject to any disclaimer, the term of this patent is extended or adjusted under 35 U.S.C. 154(b) by 0 days.

(21) Appl. No.: 15/853,538

(22) Filed: Dec. 22, 2017

Related U.S. Application Data

(60) Provisional application No. 62/599,510, filed on Dec. 15, 2017.

(51) Int. Cl.
*A61B 5/00* (2006.01)
*G01N 21/45* (2006.01)
(Continued)

(52) U.S. Cl.
CPC .......... *A61B 5/0042* (2013.01); *A61B 5/0035* (2013.01); *A61B 5/0066* (2013.01);
(Continued)

(58) Field of Classification Search
CPC .... G02B 26/06; G02B 21/0056; H04N 5/349; G01N 21/4795; G01N 21/45;
(Continued)

(56) References Cited

U.S. PATENT DOCUMENTS 3,013,467 A 12/1961 Minsky
5,625,458 A * 4/1997 Alfano ................. A61B 5/0059
356/446
(Continued)

FOREIGN PATENT DOCUMENTS

EP 1458087 B1 10/2005
EP 1771844 A1 4/2007
(Continued)

OTHER PUBLICATIONS

Al-Mujaini et al., "Optical Coherence Tomography: Clinical Applications in Medical Practice," Oman Medical Journal 28(2):86-91 (2013).

(Continued)

*Primary Examiner* — Amelie R Gillman
(74) *Attorney, Agent, or Firm* — Michael J. Bolan; Vista IP Law Group, LLP

(57) ABSTRACT

Described herein are systems and methods for noninvasive functional brain imaging using low-coherence interferometry (e.g., for the purpose of creating a brain computer interface with higher spatiotemporal resolution). One variation of a system and method comprises optical interference components and techniques using a lock-in camera. The system comprises a light source and a processor configured to rapidly phase-shift the reference light beam across a pre-selected set of phase shifts or offsets, to store a set of interference patterns associated with each of these pre-selected phase shifts, and to process these stored interference patterns to compute an estimate of the number of photons traveling between a light source and the lock-in camera detector for which the path length falls within a user-defined path length range.

27 Claims, 11 Drawing Sheets

(51) Int. Cl.
*H04N 5/349* (2011.01)
*G02B 26/06* (2006.01)
*G01N 21/47* (2006.01)
*G02B 21/00* (2006.01)

(52) U.S. Cl.
CPC ............ *A61B 5/4064* (2013.01); *G02B 26/06* (2013.01); *H04N 5/349* (2013.01); *A61B 5/0062* (2013.01); *G01N 21/45* (2013.01); *G01N 21/4795* (2013.01); *G02B 21/0056* (2013.01)

(58) Field of Classification Search
CPC ... A61B 5/0042; A61B 5/0066; A61B 5/0035; A61B 5/4064; A61B 5/0062
See application file for complete search history.

(56) References Cited

U.S. PATENT DOCUMENTS

| | | | |
|---|---|---|---|
| 5,694,938 A | 12/1997 | Feng et al. | |
| 6,041,248 A | 3/2000 | Wang | |
| 6,091,983 A | 7/2000 | Alfano et al. | |
| 6,205,353 B1 | 3/2001 | Alfano et al. | |
| 6,530,944 B2 | 3/2003 | West et al. | |
| 7,429,735 B2* | 9/2008 | Lueerssen | G01J 5/0003 250/341.8 |
| 7,498,621 B2 | 3/2009 | Seitz | |
| 7,508,505 B2 | 3/2009 | Lustenberger et al. | |
| 7,521,663 B2 | 4/2009 | Wany | |
| 7,560,701 B2 | 7/2009 | Oggier et al. | |
| 7,586,077 B2 | 9/2009 | Lehmann et al. | |
| 7,595,476 B2 | 9/2009 | Beer et al. | |
| 7,622,704 B2 | 11/2009 | Wany | |
| 7,671,671 B2 | 3/2010 | Buettgen et al. | |
| 7,701,028 B2 | 4/2010 | Alfano et al. | |
| 7,706,862 B2 | 4/2010 | Kaufmann et al. | |
| 7,884,310 B2 | 2/2011 | Buettgen | |
| 7,889,257 B2 | 2/2011 | Oggier et al. | |
| 7,897,928 B2 | 3/2011 | Kaufmann et al. | |
| 7,923,673 B2 | 4/2011 | Buttgen et al. | |
| 8,022,345 B1* | 9/2011 | Chang | G01J 9/02 250/201.9 |
| 8,103,329 B2 | 1/2012 | Fomitchov et al. | |
| 8,106,472 B2 | 1/2012 | Kaufmann et al. | |
| 8,115,158 B2 | 2/2012 | Buettgen | |
| 8,190,245 B2 | 5/2012 | Mitra | |
| 8,223,215 B2 | 7/2012 | Oggier et al. | |
| 8,299,504 B2 | 10/2012 | Seitz | |
| 8,450,674 B2 | 5/2013 | Yang et al. | |
| 8,462,355 B2 | 6/2013 | Vucinic et al. | |
| 8,525,998 B2 | 9/2013 | Yaqoob et al. | |
| 8,554,087 B2 | 10/2013 | Osterberg | |
| 8,717,574 B2 | 5/2014 | Yang et al. | |
| 8,754,939 B2 | 6/2014 | Oggier et al. | |
| 8,803,967 B2 | 8/2014 | Oggier et al. | |
| 8,922,759 B2 | 12/2014 | Gassert et al. | |
| 8,958,622 B2 | 2/2015 | Vija et al. | |
| 8,964,028 B2 | 2/2015 | Oggier | |
| 9,000,349 B1 | 4/2015 | Lehmann et al. | |
| 9,076,709 B2 | 7/2015 | Felber et al. | |
| 9,117,712 B1 | 8/2015 | Oggier et al. | |
| 9,140,795 B2 | 9/2015 | Lehmann et al. | |
| 9,195,041 B2 | 11/2015 | Redford | |
| 9,200,887 B2 | 12/2015 | Potsaid et al. | |
| 9,209,327 B2 | 12/2015 | Neukom et al. | |
| 9,313,423 B2 | 4/2016 | Wang et al. | |
| 9,329,035 B2 | 5/2016 | Oggier | |
| 9,335,154 B2 | 5/2016 | Wax et al. | |
| 9,341,715 B2 | 5/2016 | Buettgen et al. | |
| 9,435,891 B2 | 9/2016 | Oggier | |
| 9,442,196 B2 | 9/2016 | Buettgen et al. | |
| 9,555,444 B2 | 1/2017 | Goodman et al. | |
| 9,658,510 B2 | 5/2017 | Kippelen et al. | |
| 9,664,606 B2 | 5/2017 | Hajjarian et al. | |
| 9,698,196 B2 | 7/2017 | Buettgen et al. | |
| 9,730,649 B1 | 8/2017 | Jepsen | |
| 2004/0212808 A1* | 10/2004 | Okawa | A61B 1/00009 356/479 |
| 2005/0219545 A1* | 10/2005 | Chan | A61B 3/102 356/497 |
| 2006/0187533 A1 | 8/2006 | Nielsen et al. | |
| 2006/0274151 A1* | 12/2006 | Lueerssen | G01J 5/0003 348/180 |
| 2008/0024767 A1 | 1/2008 | Seitz | |
| 2008/0174785 A1 | 7/2008 | Seitz et al. | |
| 2011/0101241 A1 | 5/2011 | Cottier et al. | |
| 2011/0109962 A1* | 5/2011 | Cui | A61B 5/0059 359/385 |
| 2011/0117025 A1* | 5/2011 | Dacosta | A61B 5/0059 424/9.6 |
| 2012/0070817 A1 | 3/2012 | Wang et al. | |
| 2013/0107268 A1* | 5/2013 | Boccara | G01B 9/02 356/450 |
| 2013/0182096 A1* | 7/2013 | Boccara | A61B 5/0066 348/79 |
| 2013/0271592 A1* | 10/2013 | Piestun | H04N 7/18 348/79 |
| 2014/0176963 A1* | 6/2014 | Kemp | G01B 9/02004 356/497 |
| 2015/0320319 A1 | 11/2015 | Alfano et al. | |
| 2015/0325973 A1* | 11/2015 | Dupret | G03H 1/0005 349/1 |
| 2016/0299218 A1 | 10/2016 | Lehmann | |
| 2017/0038000 A1 | 2/2017 | Fuchsle et al. | |
| 2017/0038459 A1 | 2/2017 | Kubacki et al. | |
| 2017/0049326 A1 | 2/2017 | Alfano | |
| 2017/0090018 A1 | 3/2017 | Buettgen et al. | |
| 2017/0161890 A1* | 6/2017 | Chu | G06T 7/0008 |
| 2017/0176250 A1 | 6/2017 | Rae et al. | |
| 2018/0042480 A1* | 2/2018 | Liu | A61B 5/0066 |

FOREIGN PATENT DOCUMENTS

| | | |
|---|---|---|
| EP | 1771882 B1 | 9/2013 |
| EP | 2594959 B1 | 1/2017 |
| EP | 2815251 B1 | 3/2017 |
| ER | 2240798 B1 | 8/2016 |
| WO | WO-2006025649 A1 | 3/2006 |
| WO | WO-2006093666 A2 | 9/2006 |

OTHER PUBLICATIONS

Blanc, et al., "Smart Pixels for Real-time Optical Coherence Tomography," Proceedings of SPIE—The International Society of Optical Engineering, 13 pages (2004).

Giacomelli, M., et al., "Imaging beyond the ballistic limit in coherence imaging using multiply scattered light," Optics express 28:19(5):4268-79 (2011).

Gratton et al., "Dynamic brain imaging: Event-related optical signal (EROS) measures of the time course and localization of cognitive-related activity," Psychonomic Bulletin & Review 5(4):535-563 (1998).

HeliCam C3, retrieved on Dec. 6, 2017 on the Internet at http://www.heliotis.ch/html/lockInCameraC3.htm, 2 pages.

Horinaka et al., "Extraction of quasi-straightforward-propagating photons from diffed light transmitting through a scattering medium by polarization modulation," Optics letters 20(13):1501-3 (1995).

Kim, "Biomedical Imaging Applications of Parallel Optical Coherence Tomography and Adaptive Optics," Jeehyum Kim dissertation, The University of Texas at Austin, 168 pages (2004).

Lange, et al., "Demodulation pixels in CCD and CMOS technologies for time-of-flight ranging," InProc. SPIE 3965:177-188 (2000).

Liu et al, "Lock-in camera based heterodyne holography for ultrasound-modulated optical tomography inside dynamic scattering media," Applied physics letters 108(23):231106 (2016).

Liu et al., "Bit-efficient, sub-millisecond wavefront measurement using a lock-in camera for time-reversal based optical focusing inside scattering media," Optics letters 41(7):1321-4 (2016).

(56) References Cited

OTHER PUBLICATIONS

Matthews, et al., "Deep tissue imaging using spectroscopic analysis of multiply scattered light," Optica. 1(2):105-111 (2014).

Monte Carlo, eXtreme (MCX), retrieved on Dec. 16, 2017 from http://mcx.sourceforge.net/cgi-bin/index.cgi, 2 pages.

Patwardhan et al., "Quantitative diffuse optical tomography for small animals using an ultrafast gated image intensifier," Journal of Biomedical Optics. 13(1):011009-011009-7 (2008).

Popescu, et al., "Optical coherence tomography: fundamental principles, instrumental designs and biomedical applications," Biophys Rev 3:155-169 (2011).

Puszka et al., "Time-resolved diffuse optical tomography using fast-gated single-photon avalanche diodes," Biomedical optics express 4(8):1351-1365 (2013).

Schmitt et al., "Use of polarized light to discriminate short-path photons in a multiply scattering medium," Applied optics 31(30):6535-46 (1992).

Thrane, et al., "Complex decorrelation averaging in optical coherence tomography: a way to reduce the effect of multiple scattering and improve image contrast in a dynamic scattering medium," Opt Lett. 42(14):2738-2741 (2017).

Van der Laan et al., "Evolution of circular and linear polarization in scattering environments," Optics express 23(25):31874-88 (2015).

Wang et al.., "Three dimensional optical angiography," Optics express 15(7):4083-97 (2007).

PCT International Search Report and Written Opinion for International Appln. No. PCT/US2018/041324, Applicant HI LLC, forms PCT/USA/210, 220 and 237 dated Oct. 18, 2018 (14 pages).

Loic Blanchot, et al., "Low-coherence in-depth microscopy for biological tissue imaging: design of a real-time control system", PROC. SPIE, vol. 3194, Jan. 1, 1998 (Jan. 1, 1998), pp. 198-204.

Heliotis: "High-speed Lock-IN CMOS camera with pixel-level signal processing", Nov. 25, 2015 (Nov. 25, 2015).

Dunsby C et al: "Techniques for Depth-Resolved Imaging Through Turbid Media Including Coherence-Gated Imaging", Journal of Physics D: Applied Physics, Institute of Physics Publishing Ltd, GB, vol. 36, Jan. 1, 2003 (Jan. 1, 2003), pp. R207-R227.

\* cited by examiner

SYSTEMS AND METHODS FOR QUASI-BALLISTIC PHOTON OPTICAL COHERENCE TOMOGRAPHY IN DIFFUSIVE SCATTERING MEDIA USING A LOCK-IN CAMERA DETECTOR

CROSS-REFERENCE TO RELATED APPLICATIONS

This application claims priority to U.S. Provisional Patent Application No. 62/599,510, filed Dec. 15, 2017, the disclosure of which is hereby incorporated by reference in its entirety.

BACKGROUND

Traditional optical methods of functional human brain imaging, such as diffuse optical tomography, may be used to generate images of optical properties in the brain, which may provide information about localized neural activity, e.g., via neural activity dependent hemodynamic properties such as blood flow and/or hemoglobin oxygenation state, or other neural activity-dependent optical parameters impacting light absorption, scattering or other properties. However, because diffuse optical tomography methods typically rely on light that is randomly scattered inside the brain, the spatial resolution can be relatively limited, especially at deeper depths. The light that emerges from the brain tissue and impinges on a sensor is largely composed of multiply scattered photons that have taken a wide range of highly tortuous paths in the manner of a diffusive random walk.

Optical coherence tomography (OCT) is one example of an optical technique that can be used to image at depth inside tissue. In an OCT system, light from a low-coherence source is split into two paths along two different arms of an interferometer: a reference arm and a sample arm. Various optical components may be provided along each arm to define and/or adjust specific beam parameters, such as the shape, focal depth, and/or intensity distribution of the light. In the reference arm, the light is back-reflected by a mirror and it returns into the interference system, propagating along the same path it came from but in the opposite direction. In the sample arm, the light is backscattered through the sample medium back into the interference system. The returning light from both arms recombine or merge at a coupler to generate an interference pattern. By tuning the position of the mirror in the reference arm, the optical distance for the light propagating through the reference arm can be adjusted and the interference pattern is formed only with light that traveled, to within approximately the coherence length of the light source, the same optical distance in the sample. The dependence on optical path length of the intensity of light backscattered from beneath a sample surface can be measured based on the interference patterns resulting from varying the path length of the reference arm.

OCT has typically been applied in a microscopic mode at limited imaging depth, and in such a mode, the spatial resolution in both the axial direction (along the Z-axis) and the lateral direction (across the XY plane) may range between about 1 µm to about 10 µm, but the penetration depth (i.e., along the Z-axis) of such conventional OCT is typically only about 1-2 mm. In certain embodiments of OCT (Giacomelli M G, Wax A. "Imaging beyond the ballistic limit in coherence imaging using multiply scattered light". Optics Express. 2011 Feb. 28; 19(5):4268-79), it has been possible to image at nearly 1 cm depth with nearly 1 mm resolution. The typical thickness of a human skull, however, is from about 4 mm to about 10 mm and including the thickness of skin and any intervening dura layer, pia layer, and cerebral spinal fluid between the skull and the brain, and furthermore in order to image at depth inside the brain, an optical modality must have an imaging depth of at least 10 mm. Moreover, to operate in a tomographic mode, with source and detector located at a distance from one another on the scalp, analogous to diffuse optical tomography, an optical modality must be able to operate at several centimeters of path length between light source and light detector.

Accordingly, improvements to the penetration depth and spatial resolution of optical coherence tomography methods for imaging brain activity are desirable.

BRIEF SUMMARY

Disclosed herein are systems and methods for functional brain imaging using optical tomography. These systems and methods may comprise optical interference components and techniques and a lock-in camera to generate images of deep structures in diffusive, high-scatter media. The system may comprise a light source and a processor configured to phase-shift the reference light beam across a pre-selected set of phase shifts or offsets. The phase of the reference light beam may cycle through the entire set of pre-selected phase shifts or offsets over a time interval. In one variation, the phase is adjusted over a time interval less than the speckle decorrelation time of the desired imaging depth in the diffusive scattering medium. For example, for imaging through the human skull and into the human brain, the phase may be adjusted over a time interval less than about 1 ms or less and can be on the order of tens of microseconds (e.g., from about 5 µs to about 100 µs, about 10 µs, about 20 µs, about 40 µs, about 50 µs, about 100 µs, from about 500 µs to about 1 ms, about 800 µs, about 1 ms, etc.). The light interference pattern associated with each of the reference beam phase shifts may be detected by the lock-in camera. In one variation, the interference pattern corresponding to each phase shift or offset can be stored in the camera on a pixel-by-pixel basis. The system may then perform computations on a pixel-by-pixel basis on the set of interference patterns stored by the camera, and then average the results of those computations over all pixels to compute an estimate of the quantity of photons passing between the light source and the detector which traveled along paths within a user-determined path-length range. These systems and methods may selectively measure the optical properties of a human skull/brain based on the quantity/intensity of photons/light that have a selected path length (i.e., a path length that corresponds to the path length of the reference light beam). The light interference pattern detected by the camera is a speckle pattern, where the output of each camera detector pixel corresponds to one or more grains of the speckle pattern. For each pixel in the detector array, the processor may calculate a pixel value by calculating the absolute value of the difference in intensity values between the values stored within each pixel on the different phase shifts or offsets. The processor may then average the pixel values over all pixels to compute an estimate of the amount (e.g., intensity or amplitude) of light passing between source and detector within a selected path-length range. Changing the phase of the light beam at pre-selected shifts or offsets over a pre-selected time interval below the speckle decorrelation time associated with the desired imaging depth in the tissue may facilitate the selective detection of photons that have approximately straight travel paths in tissue (i.e., photons that have experienced some degree of scattering but have a path length that is within a light source coherence length from the path length of the reference optical path), as well as the detection of photons that have a straight travel path in tissue (i.e., photons that have a path length that matches the path length of the reference optical path). Detection of ballistic photons (e.g., photons that have a path length that matches the reference path length) and quasi-ballistic photons (e.g., photons that have a path length that approximates the reference path length within the coherence length of the light source) may help to generate images of deep tissue structures and functional activities at higher resolution as compared to traditional diffuse optical tomography methods.

One variation of an interferometry imaging system may comprise a first optical path having an adjustable path length between a lower bound and an upper bound, a second optical path, a light source configured to generate a light beam that traverses the first optical path and the second optical path, a camera comprising an array of detector pixels configured to detect an interference pattern formed by light from the first optical path and light from the second optical path, a beam combiner that merges light from the first optical path and light from the second optical path to form an interference pattern across the array of detector pixels, and a processor in communication with the camera and the light source. The camera may be a lock-in camera. The light source may be a low-coherence light source (e.g., having a coherence length of about 100 microns). The light source may be movable with respect to the camera. The second optical path may comprise a lens having a focal depth greater than or equal to the upper bound path length and a field-of-view having a width. The lower bound of the adjustable path length may be about 5 mm and the upper bound may be about 50 mm (e.g., the lower bound may be about 5 mm and the upper bound may be about 20 mm). In some variations, the first optical path may comprise a reference arm and the second optical path may comprise a sample arm. Optionally, the system may comprise a first-stage beam splitter that directs the light beam to the first optical path and the second optical path, a first circular polarizing filter disposed in the light beam between the light source and the first-stage beam splitter, and a second circular polarizing filter disposed between the beam combiner and the camera. Some variations may comprise two more cameras, each comprising an array of detector pixels.

The processor may be configured to cycle the first optical path through a plurality of pre-selected phase shifts in a predetermined time interval, to calculate a pixel value for each detector pixel by combining the pixel measurements for each of the plurality of pre-selected phase shifts, and to calculate the intensity of light from a sample depth that corresponds to the path length of the first optical path by averaging the pixel values over the detector pixel array. For example, the processor may be configured to cycle the light beam by two phase shifts and the predetermined time interval may be from about 1 μs to about 1 ms. The two phase shifts may be in increments of π. Alternatively or additionally, the processor may be configured to cycle the light beam by four phase shifts and the predetermined time interval may be from about 2 μs to about 1 ms. The four phase shifts may be in increments of π/2. The camera may be configured to detect interference pattern changes between phase-shifted light from the first optical path and phase-shifted light from the second optical path. Each detector pixel may be configured to detect two phase shifts within the time interval (e.g., each detector pixel may be configured to detect four phase shifts within the time interval). In some variations, each detector pixel may comprise a plurality of data bins configured to store light data from the interference pattern. That is, the phase of light data stored in a first data bin is different from the phase of light data stored in a second data bin. In some variations, each detector pixel may comprise two or more data bins (e.g., four data bins). Each detector pixel may have a width from about 1 μm to about 1000 μm, and/or the width of each detector pixel, after demagnification by the imaging system, may be less than or equal to a speckle grain size. The width of the field-of-view of the camera on the sample as demagnified through the imaging system may be about 1 mm.

In some variations, the processor may be configured to compute a set of per-pixel values using light data recorded by the camera during each of the plurality of pre-selected phase shifts, and may be configured to compute a sum or average of the pixel values across some or all pixels of the detector pixel array. Computing per-pixel values may comprise calculating the absolute value of the difference of two data bin values within each pixel, $|B_1[k]-B_2[k]|$ for a kth pixel. Computing the average over m pixels $Avg_{[k=1\ to\ k=m]}(|B_1[k]-B_2[k]|)$. Alternatively or additionally, for a camera comprising detector pixels that each comprise four data bins, calculating per-pixel values may comprise calculating $P_k=Sqrt[(B_2[k]-B_4[k])^2\ (B_1[k]-B_3[k])^2]/2$ for a four-bin detector pixel and then take the average over all N pixels $(1/N)*\Sigma_{k=1\ to\ k=(N)}(P_k)$.

In one variation, the light source may be a first light source and the camera may be a first camera, and the system may further comprise a second camera aligned with the first light source and a second light source aligned with the first camera. A first property of the light beam from the first light source may correspond with data from the second camera, and a second property of the light beam from the second light source may correspond with data from the first camera. For example, the first property may be a wavefront phase, and the light beam from the first light source is a phase conjugate of data from the second camera, and the second property is a wavefront phase, and the light beam from the second light source is a phase conjugate of data from the first camera.

In another variations, the light source may be a first light source and the camera may be a first camera, and the system may further comprise a second camera and a second light source. A first property of the light beam from the first light source may correspond with data from the first camera, and a second property of a light beam from the second light source may correspond with data from the first camera. For example, the first property may be a first phase value, and the second property may be a second phase value. Data from the first camera may be a first detected per-pixel phase value $\varphi_{detected}$, and the first phase value may be $(2\pi-\varphi_{detected})$, i.e., a conjugate phase value of the detected per-pixel phase value. Data from the second camera may be a second detected per-pixel phase value $\varphi_{2\_detected}$, and the second phase value may be $(2\pi-\varphi_{2\_detected})$, i.e., a conjugate phase value of the detected per-pixel phase value. In some variations, a spatial light modulator in communication with the camera may be used to emit light having the desired phase value.

One variation of a method for detecting photons for generating an image may comprise emitting a reference light signal to a reference optical path and to a sample region, where a light path through the reference optical path defines a reference path length, combining a reference light signal from the reference optical path and a sample light signal from the sample region to create an interference pattern, changing a phase of the reference light signal according to a phase shift of a set of n pre-selected phase shifts, measuring the interference pattern corresponding to each phase shift using a camera comprising an array of detector pixels, calculating a pixel value for each detector pixel of the camera by combining pixel measurements for each of the plurality of pre-selected phase shifts, and calculating the intensity of light from a sample depth that corresponds to the path length of the reference optical path by averaging the pixel values over the detector pixel array. In some variations, the set of pre-selected phase shifts may comprise three phase shifts (e.g., n=3), and the pre-selected phase shifts may be $\pi/2$, $\pi$, and $3\pi/2$. The phase changes may occur in less than about 1 millisecond or the speckle decorrelation time of the depth of interest. Calculating a pixel value may comprise quadrature detection methods. In one variation, the camera is a lock-in camera, and each detector pixel comprises one or more data bins. Measuring the interference pattern corresponding to each phase shift may comprise storing an intensity value for each phase shift in a separate pixel data bin.

BRIEF DESCRIPTION OF THE DRAWINGS

FIG. 7B is a flowchart depiction of one variation of a method. FIGS. 7C-7E depict various steps of the method of FIG. 7B.

DETAILED DESCRIPTION

Figure 1A:
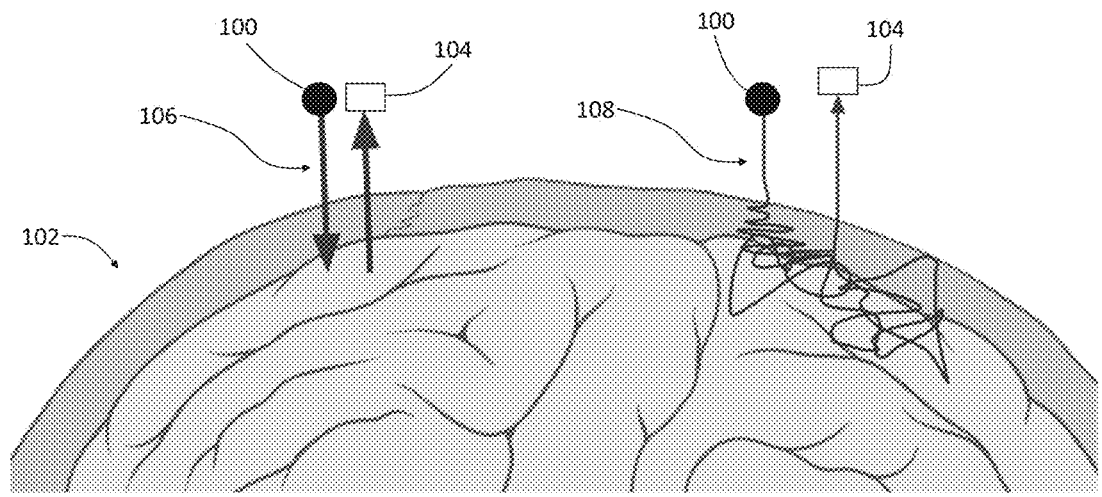
FIGS. 1A-1B are schematic representations of some optical paths of a photon through tissues of a patient's head.
Figure 1B:
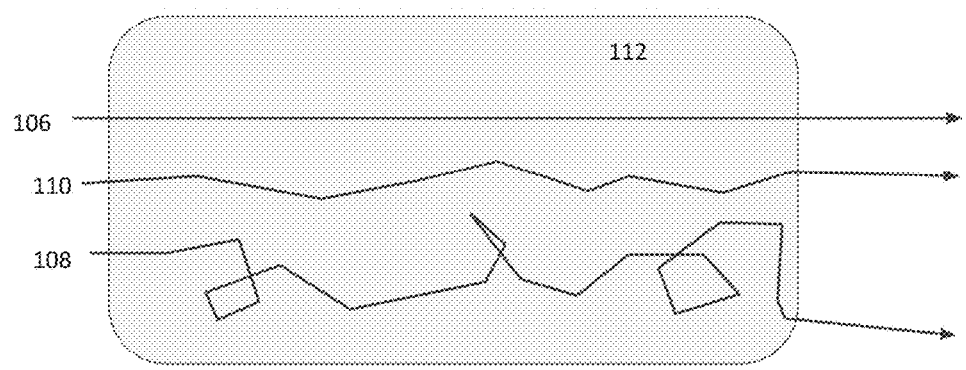

Described herein are systems and methods for functional brain imaging using low-coherence interferometry, including noninvasive functional imaging of the human brain (e.g., as part of a brain-machine interface and/or for acquiring neural data or images with higher spatiotemporal resolution as compared to diffuse optical tomography). These systems and methods may comprise optical interference components and techniques using a lock-in camera, as opposed to a conventional camera, to provide a highly efficient and scalable scheme that enables detection of highly localized and high spatial resolution signals, to generate images or tomograms of deep structures in diffusive, high-scatter media. In general, lock-in cameras include a class of digital cameras in which multiple measurements of a light field are rapidly made at each pixel in a temporally precise fashion synchronized with an external trigger or oscillation and stored in multiple "bins" within each pixel, in contrast with conventional cameras, which store only one value per pixel that merely aggregate the incoming photo-electrons over the camera frame integration time. Lock-in cameras may also perform on-chip computations on the binned values. Thus, a key feature of lock-in cameras is their ability to rapidly capture and store multiple sequential samples of the light field, with sample-to-sample latencies shorter than readout times of conventional cameras. This feature enables them, for example, to sample a modulated light field at the same frequency as the modulation, such that subtraction across successive samples will extract the component of the light that is modulated at the modulation frequency, while subtracting off the unmodulated ("DC") background. Similarly, lock-in cameras can be used to make a series of such measurements or comparisons, locked to an external trigger signal, rapidly in order to extract such modulated components from a rapidly changing light field arising from e.g., a diffusive, high-scatter media. It can be appreciated that the use of a lock-in camera provides for a high-speed and precisely timed detection method that can capture differences in a light field far faster than the frame rates of conventional cameras. While the systems described herein comprise one or more lock-in cameras, any camera that is configured to acquire multiple measurements of a light field rapidly at each pixel in a temporally-precise fashion may be used. The system may comprise a light source and a processor configured to phase-shift the reference light beam across a pre-selected set of phase shifts or offsets. The phase of the reference light beam may cycle through the entire set of pre-selected phase shifts or offsets over a time interval. In one variation, the phase of the reference light may be cycled through the entire set of pre-selected shifts or offsets faster than the speckle decorrelation time of the desired imaging depth in the diffusive scattering medium. For example, for imaging through the human skull and into the human brain, the phase may be adjusted over a time interval less than about 1 ms or less and the time interval can be on the order of tens of microseconds (e.g., from about 5 µs to about 100 µs, about 10 µs, about 20 µs, about 40 µs, about 50 µs, about 100 µs, from about 500 µs to about 1 ms, about 800 µs, about 1 ms, etc.). The light interference pattern associated with each of the phase shifts may be detected by the lock-in camera, and for each phase shift or offset, the lock-in camera will locally store the interference pattern associated with that phase shift. The system may then perform computations on a pixel-by-pixel basis on the set of interference patterns stored by the lock-in camera, and then average the results of those computations over all pixels to compute an estimate of the quantity of photons passing between source and detector which traveled along paths within a pre-selected (e.g., user-determined) path-length range. This may help to measure the optical properties of the human brain and/or skull based on the quantity/intensity of the photons/light having a pre-selected path length. The systems and methods described herein may be able to generate images of deeper tissue structures (e.g., at depths of 6 mm or more and preferably 10 mm or more) than traditional OCT, by acquiring data not only from photons that encounter little or no scatter as they traverse through tissue, but also from photons that have encountered a certain degree of scatter in tissue which causes their path lengths within the tissue to fall within a certain user-defined range. FIGS. 1A-1B illustrates some exemplary optical paths that a photon may take as it traverses from a light source (100) through hard and soft tissues of a patient's head (102) to a detector (104). FIG. 1A schematically depicts a direct or straight optical path (106) of a photon having a pre-selected path length, which may be the optical path taken by a photon that encounters little if any scatter, and a tortuous optical path (108), which may be the optical path taken by a photon that encounters multiple incidences of scatter, which may cause its path length to be much greater than that of the path (106). Traditional OCT methods detect only the photons with direct or straight optical paths (i.e., "ballistic" photons), and disregard photons that do not match the reference path length (i.e., photons that have encountered multiple incidents of scatter events). Ballistic photons may be detected by generating an interference or beat pattern by combining the light from the sample region with the reference light beam. Photons from the sample that have a path length that exceeds the reference path length do not generate an interference or beat pattern with the reference light beam, instead forming a spatially incoherent speckle pattern which is not able to be processed by the OCT system to extract information about such paths. However, this limits the imaging depth of traditional OCT methods because few photons penetrate deep into tissue and return to the tissue surface without being scattered.

Because light in brain tissue and in skull predominantly scatters in the forward direction (e.g., scattering anisotropy factor g~0.9), however, there are a minority fraction of photons, so-called "quasi-ballistic" or "snake" photons, which travel along approximately straight paths despite multiple scattering events. That is, the path length of quasi-ballistic photons may approximate a reference path length within a coherence length of the light source. FIG. 1B is a schematic depiction of the optical paths of a ballistic photon (top trace; 106), a quasi-ballistic photon (middle trace; 110), and a multiply-scattered photon (bottom trace; 108) through a sample of skull and/or brain tissue (112). The path length of the ballistic photon (106) may match a pre-selected path length (L), i.e., path length of a reference optical path. The path length of the quasi-ballistic photon (110) may be (L+$\Delta$L), where $\Delta L < L_{coherence}$, where $L_{coherence}$ is the coherence length of the light source. The path length of the multiply-scattered photon (108) may also be (L+$\Delta$L), but where $\Delta L \gg L_{coherence}$. The systems and methods described herein are configured to select for ballistic and quasi-ballistic photons for generating images of structures deeper beneath the tissue surface and/or may improve the spatial resolution such images as compared to traditional OCT methods.

One variation of a system configured to selectively detect quasi-ballistic photons to generate images of deep structures in diffusive, high-scatter tissue media (e.g., such as the human skull and brain, through the thickness of the human skin and skull and into cerebral cortical brain tissue) may comprise a low-coherence light source, one or more lock-in cameras, and a processor in communication with the light source and the one or more lock-in cameras. The one or more lock-in cameras may each comprise an array of detector pixels that detect ballistic photons and/or quasi-ballistic photons on the basis of path length. In some variations, the entire area of the lock-in camera may be configured to measure the optical properties of a tissue volume-of-interest located along a selected optical path (e.g., a path that enters into brain tissue grey matter that illuminates only a single target voxel) at any given time, measuring the full wavefront holographically to enable greater imaging depth in strongly scattering media through the use of ballistic and/or quasi-ballistic photons.

In some variations, a low-coherence interferometry imaging system comprising a lock-in camera may be used to select for ballistic and/or quasi-ballistic photons based on path-length matching. Quasi-ballistic photons (110) such as those depicted in FIG. 1B may be selected by adjusting the path length of the reference beam (i.e., the reference path length) by a set of pre-selected offsets or phase shifts. An interference pattern may be formed by combining light of the reference beam and light that has traversed through the sample that has a light path that approximately matches, to within the coherence length of the light source, the path length of reference beam. Otherwise, the incoherence of the light source randomizes any interference that would occur. The processor may adjust the reference beam path length to have a pre-selected set of phase shifts. The pre-selected set of phase shifts comprise a plurality of shifts or offsets that differ from each other in equal intervals (e.g., evenly spaced), or may differ from each other in variable intervals (e.g., the difference between the shifts may be vary between the shifts). The known values of these phase shifts may facilitate path length-selective detection of photons by spatially-resolved measurement by the lock-in camera of a speckle pattern that results from multiple scattering events inside a diffusive, high-scatter tissue medium. The speckle pattern may be measured by an array of camera detector pixels, and the speckle pattern measurements may be analyzed by a processor to identify photons that have a selected path length. In some variations, each detector pixel may correspond to a grain of the speckle pattern. The light field resulting from quasi-ballistic photon paths inside a high-scatter medium may be strongly scattered (relative to low-scatter media, such as in ocular structures and/or through air), resulting in a random pattern of scattered light on the surface of the brain. A speckle pattern can be phase-incoherent across speckles (an example of which is depicted in FIG. 5C). In some variations, the pixel size of the lock-in camera used for wavefront measurement be selected to correspond with the speckle grain size from a given depth of interest (e.g., pixel size may be matched approximately to the speckle grain size by a magnification system). The full amplitude of the beat pattern recorded on the lock-in camera may be extracted and may be used to calculate the number of quasi-ballistic photons traveling between light source and camera that have a path length that matches the reference path length. By measuring this amplitude at each speckle grain for each phase shift or offset with a lock-in camera, and then averaging the resulting amplitude across all pixels or speckle grains, the number of quasi-ballistic photons may be calculated despite the spatial incoherence of the speckle phases. The lock-in camera may be used to sensitively detect phase dependent interference terms while suppressing constant background terms. Alternatively or additionally, an imaging system may comprise a demodulation camera and may use homodyne holography methods to measure the full wavefront and/or aggregate amount of quasi-ballistic light scattered from the tissue. Expanding the collection of light data to include both ballistic and quasi-ballistic photons may extend optical coherence-based path length selection to large diffusive, high-scatter tissue media.

A light source may generate light having any desired coherence length. In some variations, a light source may have a coherence length of about 100 μm for imaging structures about 6 mm or more into tissue (e.g., about 6 mm, about 7 mm to about 8 mm, about 8 mm to about 10 mm, about 8 mm below the surface of the scalp, through the skull, and into cortical tissue). In other variations, a light source may have a coherence length of about 120 μm, about 130 μm, about 150 μm, about 200 μm, or more. The spatial resolution of these systems and methods at depths of about 6 mm or more may be about 1 mm. A light source that may be used in a low-coherence interferometry imaging system may be any low-coherence laser source with a coherence length chosen to correspond to the desired level of path-length selectivity. Other examples of low-coherence light sources that may be used in any of the systems described herein may include a super luminescent diode (SLD), a light emitting diode (LED), a Ti: Saph laser, a white light lamp, a diode-pumped solid-state (DPSS) laser, a laser diode (LD), a light emitting diode (LED), a super luminescent light emitting diode (sLED), a titanium sapphire laser, and/or a micro light emitting diode (mLED), among other light sources. The wavelength(s) of light generated by a light source may vary between about 350 nm to about 1.5 um, and/or may be UV light, visible light, and/or near-infrared and infrared light. The light source may generate monochromatic light comprising single-wavelength light, or light having multiple wavelengths (e.g., white light). In some variations, a light source can emit a broad optical spectrum or emit a narrow optical spectrum that is then rapidly swept (e.g., changed over time) to functionally mimic or create an effective broad optical spectrum.

The imaging systems described herein can select photons which traverse along an approximately straight line through the skull from a known source position, into a known small voxel of the brain (e.g., on the order of 1 mm in size) and then straight back out again to a lock-in camera detector at a known position. Based on the knowledge that the paths traveled by the photons were approximately straight, the absorption along the path can be attributed specifically to known small voxels of brain tissue, thus effectively gaining higher spatial resolution in measurement of the optical absorption in brain tissue. This optical absorption may be used to determine functional and activity-dependent properties of the voxel of interest in the brain. Such system and method may help to improve the spatial resolution, and/or the sensitivity to small and/or fast localized signal changes, in diffuse optical tomography-based functional brain imaging.

Systems

System Overview

One variation of a low-coherence interferometry imaging system that may be used for non-invasive brain imaging may comprise a first optical path (e.g., a reference beam path), a second optical path (e.g., a sample beam path), a low-coherence light source, and a processor in communication with a camera and the light source. The processor may be configured to cycle the path length of the first optical path (e.g., reference path length) through a plurality of pre-selected phase shifts or offsets in a predetermined time interval. The interference patterns generated from the reference beam and the light that has interacted with the tissue (e.g., that has traversed through the scalp, skull, brain, and back) may be detected by the camera in the form of a speckle pattern. The speckle pattern measurements may be an aggregate of the outputs of an array of camera detector pixels (e.g., where each detector pixel corresponds to a grain of the speckle pattern). In some variations, the camera may be a lock-in camera comprising an array of detector pixels. Each detector pixel may comprise one or more data bins configured to store pixel intensity data or intensity values. For example, a detector pixel comprising a plurality of data bins may allow the pixel to store pixel intensity data from multiple time points. In one variation, images of structures that are about 6 mm or more below the surface of the skin may be generated by performing computations on the plurality of speckle pattern intensity data stored by the lock-in camera at each pixel (e.g., computing the absolute value of the difference of the pixel intensity values in each data bin together to generate a pixel value), and then averaging the results of those computations (e.g., averaging the pixel value) over all pixels of the camera to obtain an estimate of the number of path-length-selected photons (e.g., quasi-ballistic and/or ballistic photons having a selected path length) which have traveled between the light source and the lock-in camera while ignoring counts of other photons (e.g., photons or light having a path length that differs from the selected path length). Path length selection may be implemented by adjusting the reference path length. In one variation of the invention, the lock-in camera will store at each pixel the value the intensity at a particular speckle grain of the interference pattern formed by the light exiting the sample and a particular phase shift of the reference light beam. A pixel value for each pixel may be calculated by combining the stored interference measurements from each (different) phase. The pixel value may represent the intensity or number of photons which have traveled along the path-length-selected paths. Interference terms arising from photons with other path lengths, e.g., multiply-scattered photons, may be reduced or eliminated by combining interference measurements of different phases or offsets. The pixel value at each pixel may represent an estimate of the total number of photons that have traversed between the low-coherence light source and lock-in camera's field-of-view (which may be about 1 mm in size or less, for example, from about 0.25 mm to about 1 mm) along path-length-selected paths.

The dimensions of each detector pixel may be from about 0.5 μm to about 100 μm, which may be matched via an appropriate magnification system to approximately the size of a speckle grain. In some variations, an unmagnified speckle grain of a fully developed speckle pattern may be a fraction of the wavelength of the light used, e.g., with a typical speckle grain size on the order of about 300-500 nm for near-infrared light.

Some variations of a low-coherence interferometry imaging systems may comprise a light source and a lock-in camera that are located adjacent to each other (e.g., co-localized) over a region of a patient's scalp, similar to the relative positions of the light source (100) and detector (104) depicted in FIG. 1A. For example, the light source and lock-in camera may be located between about 0.5 mm to about 2.5 cm apart from each other and/or may be included in the same device housing and/or may be arranged such that the field-of-view of the camera is illuminated by the light source or emitter and/or spatial light modulator. Alternatively, the light source may not be located adjacent to (e.g., co-localized with) the lock-in camera (e.g., may be located about 3 cm or more apart from each other), however, a light emitter in optical communication with the light source may emit light adjacent to (e.g., co-localized with) the lock-in camera. For example, the light source may be a source of the appropriate coherence length (such as any of the low-coherence light sources described above) and the emitter may be one or more optical fibers that extend between the light source and the surface of the target region of interest. There may be little or no lateral distance between the light source (and/or light emitter) and the lock-in camera. Alternatively or additionally, some systems may comprise a plurality of lock-in cameras and/or light sources, which may be mounted or placed at various locations on a patient's scalp, for example, at locations that correspond with brain regions of interest. The lock-in camera(s) and light source(s) may be located at a distance from each other, i.e., having a lateral distance between the light source(s) (and/or light emitter(s)) and the lock-in camera(s). Optionally, a light source may be movable across the surface of the patient's scalp, thereby varying the lateral distance between the one or more lock-in cameras. The location of each lock-in camera and the light source may be stored in the processor so that the reference path length and the speckle pattern measurements or data from each of the lock-in cameras may be used to calculate intensity values that represent the levels of optical absorption or scattering by structures beneath the scalp, e.g., beneath the skull, and/or in the cerebral cortical brain tissue.

Alternatively or additionally, a system may comprise a first optical assembly comprising a first light source or emitter, a first lock-in camera co-localized with (e.g., adjacent to) the first light source, and a second optical assembly comprising a second light source or emitter, and a second lock-in camera co-localized with (e.g., adjacent to) the second light source. Each optical assembly may comprise a device housing that contains the light source and lock-in camera. For example, each light source and its corresponding lock-in camera may be located between about 0.5 mm to about 2.5 cm apart from each other and/or may be arranged such that the field-of-view of the camera is illuminated by the light source. Each light source may be in communication with its corresponding lock-in camera such that data from the lock-in camera can be used to adjust the optical properties of the light source. Alternatively or additionally, an optical assembly may comprise a spatial light modulator, and data from the lock-in camera can be used to the adjust the optical properties of the light emitted from the spatial light modulator. The spatial light modulator may be located between about 0.5 mm to about 2.5 cm apart from the lock-in camera and/or may be arranged such that the field-of-view of the camera is illuminated by the spatial light modulator. The first light source and lock-in camera may be placed at a first location on a patient's scalp and the second light source and lock-in camera may be placed at a second location on the scalp, where the second location is laterally separated from the first location. The second lock-in camera may be used to measure ballistic and/or quasi-ballistic photons that have traversed through the tissue sample from the first light source. An optical property of the ballistic and/or quasi-ballistic photons detected by the second lock-in camera (e.g., the number of the such path-length-selected photons, phase, and/or amplitude data) may be extracted by the processor. For example, the full wavefront of the path-length-selected photons may be measured, and the processor may compute a phase conjugate amplitude and/or phase pattern for display on a spatial light modulator. The light source may produce a phase-conjugated copy of the path-length-selected wavefront, so as to generate additional path-length-selected photons. For example, the system may comprise a first spatial light modulator located in the optical path of the first light source and a second spatial light modulator located in the optical path of the second light source. The light sources may each illuminate the corresponding spatial light modulator to produce a phase-conjugated copy of the path-length-selected wavefront to the patient's scalp. This may result in an increased yield of path-length-selected photons. In turn, this increased number of path-length-selected photons may be used to probe or interrogate tissue structures at a tissue depth that corresponds to the reference path length. Furthermore, increased number of path-length-selected photons that have traversed through the tissue sample from the second light source and spatial light modulator assembly may be detected by the first camera, which may in turn be used to measure the full wavefront of the path-length-selected photons, and the processor may compute a phase conjugate amplitude and/or phase pattern for illumination on the first light source and spatial light modulator assembly. A phase-conjugated copy of the path-length-selected wavefront produced by the first light source and spatial light modulator assembly may illuminate the patient's scalp, so as to generate further additional path-length-selected photons. This process may be iteratively repeated to progressively increase the number of path-length-selected photons on each back-and-forth pass between the first light source/camera/spatial light modulator assembly and the second light source/camera/spatial light modulator assembly.

Figure 2:
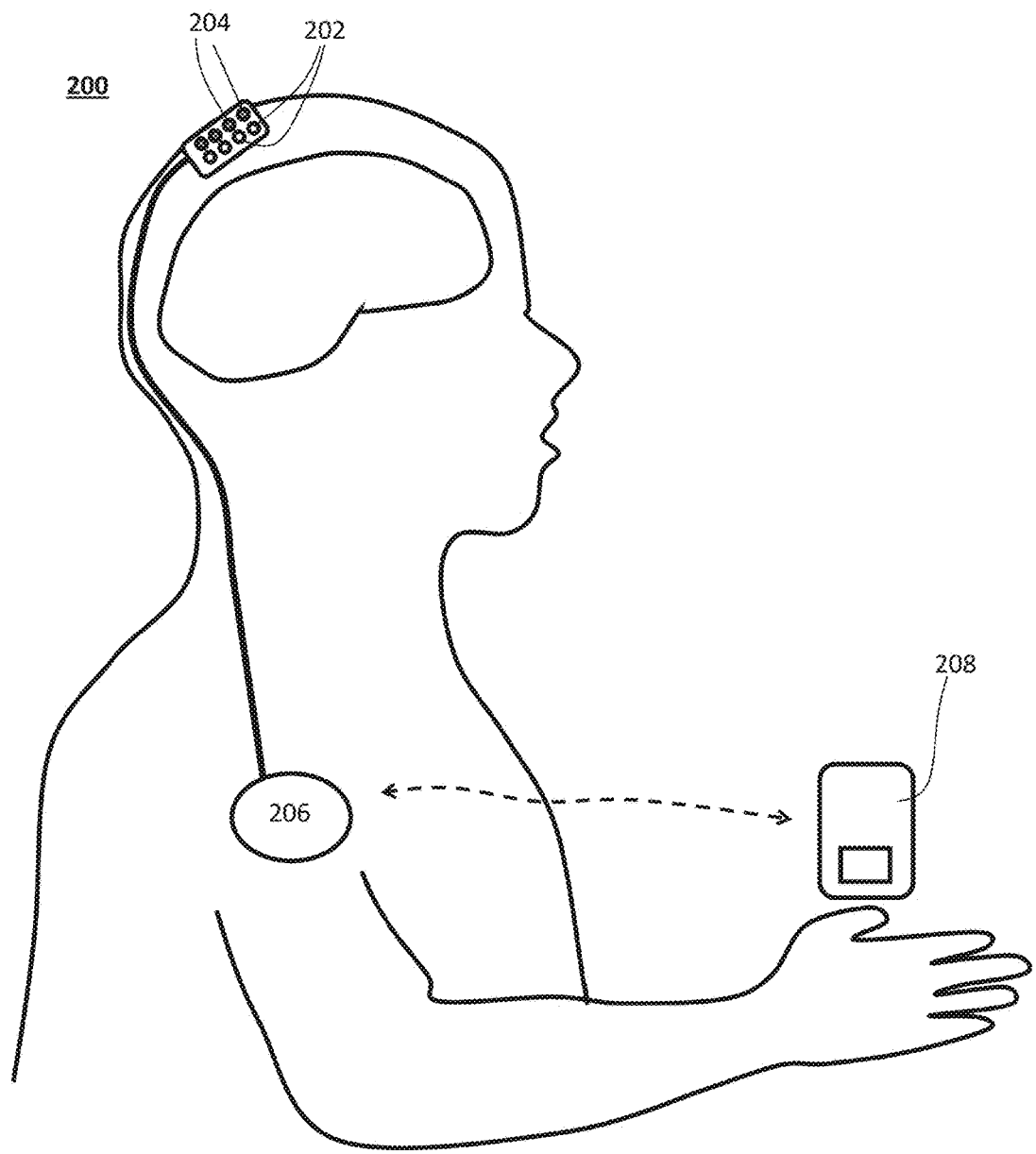
FIG. 2 is a schematic depiction of one variation of a non-invasive brain imaging system.

FIG. 2 is a schematic depiction of one variation of a non-invasive brain imaging system, such as any of the low-coherence interferometry imaging systems described herein. The imaging system (200) may comprise one or more cameras (202) configured to be attached to a patient's skull, one or more light sources (204), and a processor (206) in communication with the camera(s) (202) and the light source(s) (204). The system (200) may also comprise a reference optical path and a sample optical path (not shown) between the light source(s) (204) and the camera(s) (202). The processor (206) may be located on the patient's scalp, neck, shoulders, chest, or arm, as may be desirable. The processor (206) may be connected to the camera(s) and light source(s) via one or more wires, and/or via wireless connection protocols. The system (200) may optionally comprise a remote processor (208) in communication with the patient-mounted processor (206). The remote processor (208) may store image data from the camera(s) and/or patient-mounted processor from previous sessions, for example. Power for the light source(s), camera(s), and/or patient-mounted processor may be provided via a wearable battery. For example, the processor and battery may be enclosed in a single housing, and wires from the processor and the battery may extend to the light source(s) and camera(s). Alternatively, power may be provided wirelessly (e.g., by induction). In some variations, the processor may be integrated in the same assembly as the cameras (202) and light sources (204), for example, enclosed in the same housing. The camera(s) (202) may consist of lock-in camera(s).

Figure 3A:
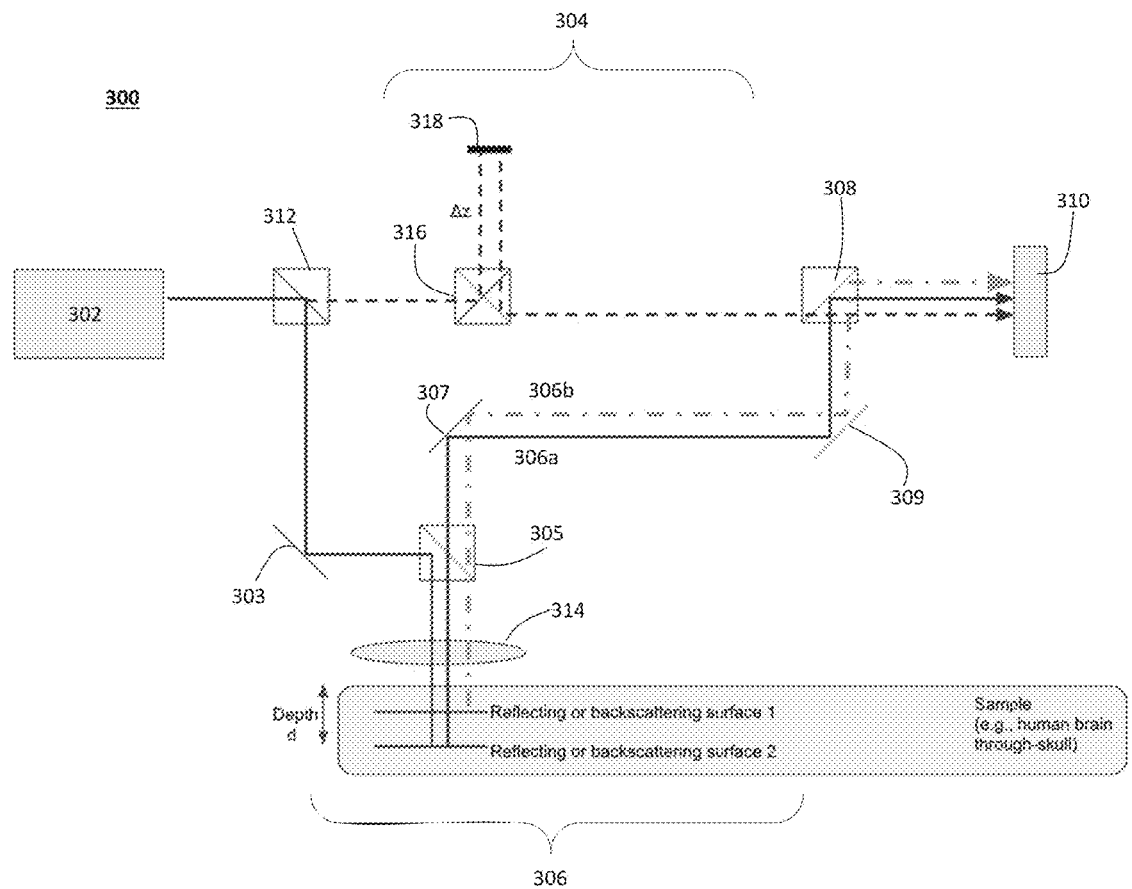
FIG. 3A is a schematic depiction of one variation of a low-coherence interferometry imaging system comprising a lock-in camera.

FIG. 3A is a schematic depiction of one variation of a first optical path (e.g., a reference optical path) and a second optical path (e.g., a sample optical path) of a low-coherence interferometry imaging system comprising a lock-in camera. The system (300) may comprise a light source (302) configured to generate a low-coherence light beam, a first optical path (304) (e.g., a reference beam path), a second optical path) (306) (e.g., a sample beam path), a combiner (308) that merges light from the first and second optical paths to form an interference pattern, and a camera (310). The camera may be a lock-in camera that detects the interference patterns from the combiner (308) to generate a speckle pattern measurement. The light source (302) may generate light with a low coherence length (e.g., $L_{coherence}$ of FIG. 1B), for example, a coherence length from about 75 μm to about 200 μm, e.g., about 100 μm. The light beam from the light source (302) may be split by a beam splitter (312) into two beams, one of which passes through the first optical path (304) (e.g., reference beam path), and the other through the second optical path (306) (e.g., sample beam path into the tissue sample or skull). The first optical path (304) may comprise a beam splitter (316) and a movable mirror (318), where the reference path length can be adjusted by moving the mirror (318) with respect to the beam splitter (316). Light from the first optical path (304) may generate an interference pattern with light from the second optical path (306) that selects for photons that have a path length that is the same as the reference path length (represented by the solid line (306a)). The distance (Δz) between the mirror (318) and the beam splitter (316) may be varied such that the reference path length is varied between a lower bound of about 5 mm and an upper bound of about 50 mm (e.g., reference path length may vary from about 5 mm to about 20 mm, from about 5 mm to about 50 mm, etc.). In some variations, the reference path length may be adjustable both in coarse and fine increments. For example, it may first be adjusted coarsely such that only photons traveling through the sample along a set of quasi-ballistic paths with a certain length between the light source and the camera are selected due to their length match with the reference path length to within the light source coherence length. Other photons may have path lengths that differ from the reference beam path length by more than the light source coherence length (e.g., represented by the dotted line (306b)) and therefore do not generate significant measured interference signals after detection and processing by the lock-in camera detector and processor.

The second optical path (306) or sample beam path may comprise a plurality of mirrors, and/or beam splitters, and/or lenses that direct light into a tissue sample. For example, the second optical path (306) may comprise a first mirror (303) that directs light from the beam splitter (312) to a second beam splitter (305). The second beam splitter (305) directs light to a lens (314) that shapes the light beam into the tissue sample. The lens (314) may have a focal depth that is at least as long as the upper bound of reference beam path length, e.g., about 10 mm. The lens (314) may optionally have a field-of-view with a diameter from about 0.25 mm to about 2 mm, e.g., about 1 mm. The relative locations of the light source (302) and the camera (310) may be selected such that the sample region of interest is located along a selected path length between the light source and the camera. Alternatively or additionally, the lens (314) may be a collimating lens. Light that traverses the second optical path (306) or sample beam path may enter the sample and some of the photons may be scattered multiple times while penetrating into and reflecting out of the tissue. In some variations, light from the tissue may pass through the lens (314) and the second beam splitter (305) to a second mirror (307) and a third mirror (309) to the combiner (308). Alternatively or additionally, light from the tissue may be collected using optical fibers, and/or light from the tissue that has been optically modified by the lens (314) may be delivered to the combiner (308) via one or more optical fibers or lightguides. Light from the second optical path (306) (e.g., sample beam path returning from the tissue) may be combined with light from the reference beam path at the combiner (308) to create an interference or beat pattern that is measured by the camera (310). The scattered light leaving the sample along second optical path (306) may include light components with many different path lengths. For example, as depicted in FIG. 3A, some photons may travel approximately straight paths reflecting or scattering off of layers at two different depths in the sample (e.g., ballistic photons). Other photons may differ in the degree to which they deviate from a linear or ballistic path in and out of the sample (e.g., quasi-ballistic photons). Ballistic and/or quasi-ballistic photons may be selected based on the interference pattern they form with light from the reference beam path. That is, photons exiting the tissue sample with a path length that matches the reference path length (or a selected path length) may form interference patterns with the light from the reference beam path, and the resulting interference patterns may be measured by the lock-in camera (310). The camera (310) may be in communication with a processor that stores and analyzes the camera output values. In some variations, a processor performs calculations that may reject background light that arises from the non-path-length-selected paths and/or facilitate a high signal-to-noise ratio measurement of the number of quasi-ballistic and/or ballistic photons (i.e., photons traveling along the path-length-selected paths). A selected path length, for example, may correspond to photons whose total path length into and out of the tissue sample matches the reference path length to within the coherence length of the light source.

The light field that is detected by the camera (310) may be a speckle pattern, with each speckle grain containing light having a random phase offset and/or background scatter. Extracting the amplitude or intensity of ballistic and/or quasi-ballistic light may comprise eliminating (e.g., ignoring) and/or reducing the contribution of this random phase offset and/or background scatter. In one variation, the amplitude or intensity of quasi-ballistic light may be selected by varying the phase of the light in the reference beam path with a plurality of pre-selected phase shifts or offsets. Changes in the interference pattern due to these phase shifts or offsets may be detected by the camera (310). In some variations, the camera (310) may comprise a lock-in camera comprising an array of detector pixels configured to detect a changing interference pattern in relatively short time intervals, which in one variation, may be less than the speckle decorrelation time of the selected imaging depth within the tissue (e.g., less than 1 millisecond for imaging more than 3 mm into living brain tissue, and less than 100 microseconds for imaging through the skull and into the cortical brain tissue underneath). The detector pixels may be configured to measure and store at each pixel several frames in short succession, time-locked to the introduction of the small phase offsets in the light traversing through the reference beam path, so as to measure and store each of several interferences between the quasi-ballistic light emerging from the sample and the reference beam path under the several different pre-selected phase offsets. These several measurements can then be combined to calculate the amplitude of the quasi-ballistic photon fraction, in spite of the unknown phase offset and background, for example according to the known principles of quadrature detection. In one variation, the lock-in camera will store at each pixel the value the intensity at a particular speckle grain of the interference pattern formed by the light exiting the sample and a particular phase shift of the reference beam.

The light source or emitter (302) and the camera (310) may be located adjacent to each other (e.g., co-localized) over a region of a patient's scalp, similar to the relative positions of the light source (100) and detector (104)

depicted in FIG. 1A. For example, the light source or emitter may be located between about 0.5 mm to about 2.5 cm apart from the lock-in camera and/or may be arranged such that the field-of-view of the camera is illuminated by the light source or emitter modulator. Alternatively, the light source (302) may not be located adjacent to (e.g., co-localized with) the camera (310), however, a light emitter in optical communication with the light source may emit light adjacent to (e.g., co-localized with) the camera. For example, the light source may be a source of the appropriate coherence length (e.g., any of the low-coherence light sources described above, which may be located remotely from the detector), and the emitter may be one or more optical fibers that extend between the light source and the surface of the target region of interest. There may be little or no lateral distance between the light source (and/or light emitter) and the camera. Alternatively, the camera (310) and light source (302) (or light emitter) may be located at a distance from each other, i.e., having a lateral distance between the light source(s) (and/or light emitter(s)) and the camera(s).

Camera

Some variations comprise a lock-in camera configured to selectively extract path-length-selected photons (or equivalently, time-of-flight-selected photons) from the speckle pattern resulting from light scattering in a large, highly scattering medium containing many scattering events. A lock-in camera may comprise an array of detector pixels. The measured speckle pattern may be an aggregate of the outputs of the array of detector pixels, where each detector pixel corresponds to a grain of the speckle pattern for a selected depth of interest (e.g., the pixel size may be matched approximately to the speckle grain size by a magnification system). The field-of-view of each detector pixel may have a size from about 300 nanometers to 50 microns and/or may correspond to the size of each grain of the speckle pattern. In some variations, a lock-in camera may comprise a microchip containing an array of detector pixels. Some variations may comprise a plurality of microchips, where each microchip has an array of detector pixels. The greater the number of detector pixels in a lock-in camera, the greater the sensitivity and signal to noise ratio of the detection process. For greater signal to noise ratio, in turn, more stringent path length selection may be applied, resulting in fewer detected photons while also achieving a higher spatial resolution, e.g., a higher degree of spatial confinement of path-length-selected paths for which optical properties of the tissue will be selectively measured. Some variations of a lock-in camera may comprise on the order of ninety thousand to one million or more detector pixels (on a single microchip or across multiple microchips). A microchip-based lock-in camera may be compatible with miniaturization for mounting or wearing on a patient's head. In some variations, an interferometry imaging system may comprise an array of multiple lock-in camera microchips on a common circuit board or mounting substrate. The circuit board may be flat, angled, or curved to match the approximate shape of a patient's skull. In some variations, the circuit board may be a flexible printed circuit board and/or may comprise a series of hinged board portions or segments such that the array of lock-in camera chips conforms to the surface curvature of the patient's head. Each of the lock-in camera chips may have a separate optical path length setting to reflect the different positions of each of the lock-in camera chips to the reference optical path.

In some variations, a lock-in camera may comprise a plurality of detector pixels that each have a size or field-of-view of each detector pixel that corresponds to the size of a speckle grain. A speckle grain may be measured by one or more detector pixels. The size of a speckle grain may vary depend on the optical properties of the tissue(s) and/or the depth of the structure of interest beneath the tissue surface. For example, the speckle grain size for brain tissue may be different from the speckle grain size for muscle tissue due to the different optical properties of brain tissue and muscle tissue. Furthermore, the speckle grain size for a structure at a depth of 3 mm in brain tissue may be different from the speckle grain size for a structure at a depth of 7 mm in brain tissue. Lock-in cameras with different detector pixel properties (e.g., size of field-of-view or receptive field, integrated collection optics, number of data bins, data receive and transmit rates, etc.), or magnification systems with different magnifications, may be selected depending on the tissue type and the depth of the region of interest within the tissue.

As described above, the pre-selected phase shifts or offsets in the reference light beam (i.e., light traversing the first optical path or reference beam path) may be cycled through in a relatively short time interval, for example, in about 1 ms or less, and/or within the speckle decorrelation time of the speckle pattern (which may vary depending on the characteristics of the tissue). A lock-in camera can acquire a succession of multiple measurements at multiple defined phase offsets within a similar time interval, storing the results of each measurement within several electronically separate storage bins within each pixel. If the measurements for each of the pre-selected phase offsets or shifts are not acquired within the speckle decorrelation time, then changes in the random phase offset and/or background scatter may corrupt or hinder the ability to extract the amplitude of the quasi-ballistic photon fraction via the described lock-in camera based detection and processing pipeline.

In one variation, a set of pre-selected phase shifts or offsets may comprise two phase shifts or offsets (e.g., 0, $\pi$), or four phase shifts or offsets (e.g., 0, $\pi/2$, $\pi$, $3\pi/2$). In other examples, a different size or number of offsets may be used, or may be dynamically adjusted during imaging. Therefore, within the speckle decorrelation time for the desired imaging depth in the tissue, the reference light beam cycles through these two or four phase shifts and the lock-in camera acquires the interference pattern for each of these phase shifts. Each detector pixel of a lock-in camera comprises multiple data bins that can store data in rapid succession, in a temporally-precise fashion synchronized with an external trigger or oscillation signal (e.g., provided by a system processor). In contrast, conventional cameras only store one value per pixel that is merely an aggregate of the incoming photons over the camera frame integration time. In some variations, a detector pixel may comprise two data bins where data from a first phase shift or offset is stored in the first data bin and data from a second phase shift or offset is stored in the second data bin. A detector pixel may comprise four or more data bins where data from a first phase shift is stored in the first data bin, data from a second phase shift is stored in the second data bin, data from a third phase shift is stored in the third data bin, and data from a fourth phase shift is stored in the fourth data bin. Data from the detector pixels may be transferred to a memory (e.g., a processor memory) for later analysis and/or aggregation with other imaging data. For example, data transfer from the lock-in camera detector pixels to a processor memory may occur after the pixel data bins are full, and/or at a rate that is less than the rate at which the camera acquires the multiple bins of image data (e.g., about half the lock-in camera bin-to-bin acquisition rate, about a quarter the lock-in camera bin-to-bin acquisition rate, etc.).

Multi-Camera System

One variation of an interferometry imaging system may comprise a plurality of lock-in cameras at different locations on the skin surface and one or more movable light sources. Moving a light source across the skin surface in a pattern around the plurality of lock-in cameras may distribute light into the tissue from various locations on the tissue surface. The photons may be reflected and/or backscattered to the tissue surface and detected by the plurality of lock-in cameras at different locations. The interference patterns detected by each of the plurality of lock-in cameras and the corresponding speckle pattern measurements or data from the lock-in cameras may be used to select for ballistic and/or quasi-ballistic photons. For example, speckle pattern measurements or data from the lock-in cameras may be used to select for photons emitted from the various locations of the moving light source(s) to each of the plurality of lock-in cameras having a pre-selected path length. Distributing light into the skull from various locations along the scalp may provide photons that take a set of multiple optical paths that "criss-cross" through brain tissue in the manner of a "checkerboard", and/or take a set of optical paths with multiple triangular or curved pathways arranged in rows and columns or in other multi-source/multi-detector configurations comprising tilings of the region of interest in the tissue along multiple axes in the manner of tomographic data collection. These optical paths may first pass through skin and skull along a relatively straight path, then briefly enter the brain tissue, then exit along a relatively straight path. Photons that traverse along multiple "criss-crossed" optical pathways may facilitate the generation of a high-resolution functional map of the upper layer of cortex with a spatial resolution given by the XY (i.e., along the plane of the scalp) confinement of the paths and not limited by their lower Z confinement, in the manner of tomographic volume reconstruction. In this method, defining the lateral cross section of a bundle of quasi-ballistic photon paths between a given source and detector as XY and the axial direction along the optical paths as Z. Moving the light source with respect to one or more cameras (e.g., lock-in cameras) at one or more pre-determined locations may probe a region of interest from multiple angles and directions. Photons that have a selected path length (e.g., ballistic and/or quasi-ballistic photons) that traverse a plurality of directions and are detected by cameras at different locations may provide optical data of a region of interest along multiple axes. Optical data taken across multiple axes across a region of interest may facilitate the generation of a 3-D map of the region of interest. Optical data from overlapping photon paths may also help to improve the resolution of the region of overlap. Speckle pattern measurements or data from the plurality of lock-in cameras may be used to generate images with comparable resolution in the Z-direction (e.g., perpendicular to a tissue surface) as in the XY-plane (e.g., along the tissue surface), and/or may allow optical probing or interrogation of a larger region in brain tissue (e.g., across multiple voxels, over a surface of the scalp).

Figure 4A:
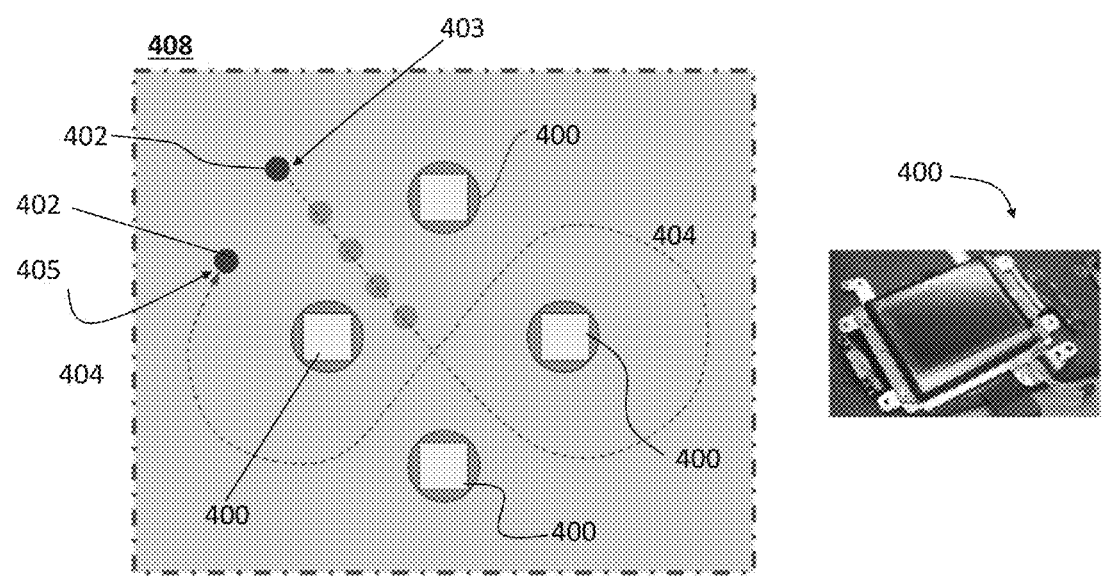
FIG. 4A depicts one variation of a system comprising multiple lock-in cameras and a low-coherence light source that is movable relative to the lock-in cameras.
Figure 4B:
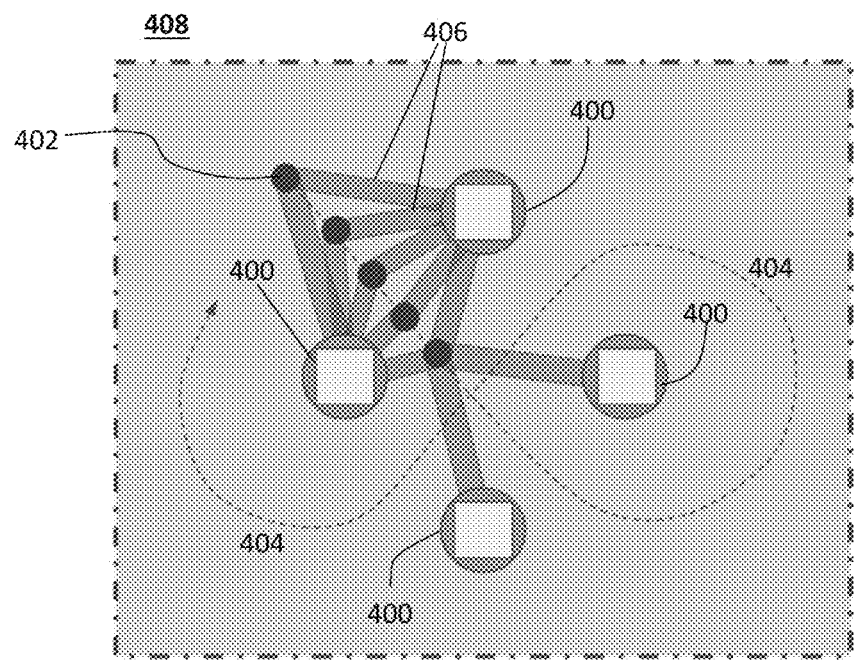
FIG. 4B depicts a series of triangular or curved optical paths through brain tissue.

FIG. 4A depicts a top view of one variation of a system comprising one or more lock-in cameras (400) located at fixed positions on the head or scalp (408), and a movable low-coherence light source (402), e.g., a laser source. The dotted lines represent a series of steps or locations to which the low-coherence light source (402) may be moved (e.g., from a first location (403) to a second location (405)). The light source (402) may be moved along a path or a pattern (404) that changes its position relative to the multiple cameras (400) over time. The light source motion may be continuous or stepped. This may result in a series of triangular or curved paths (406) through brain tissue under the scalp (408) being interrogated while the laser spot moves along the path (404), as depicted in FIG. 4B.

Figure 4C:
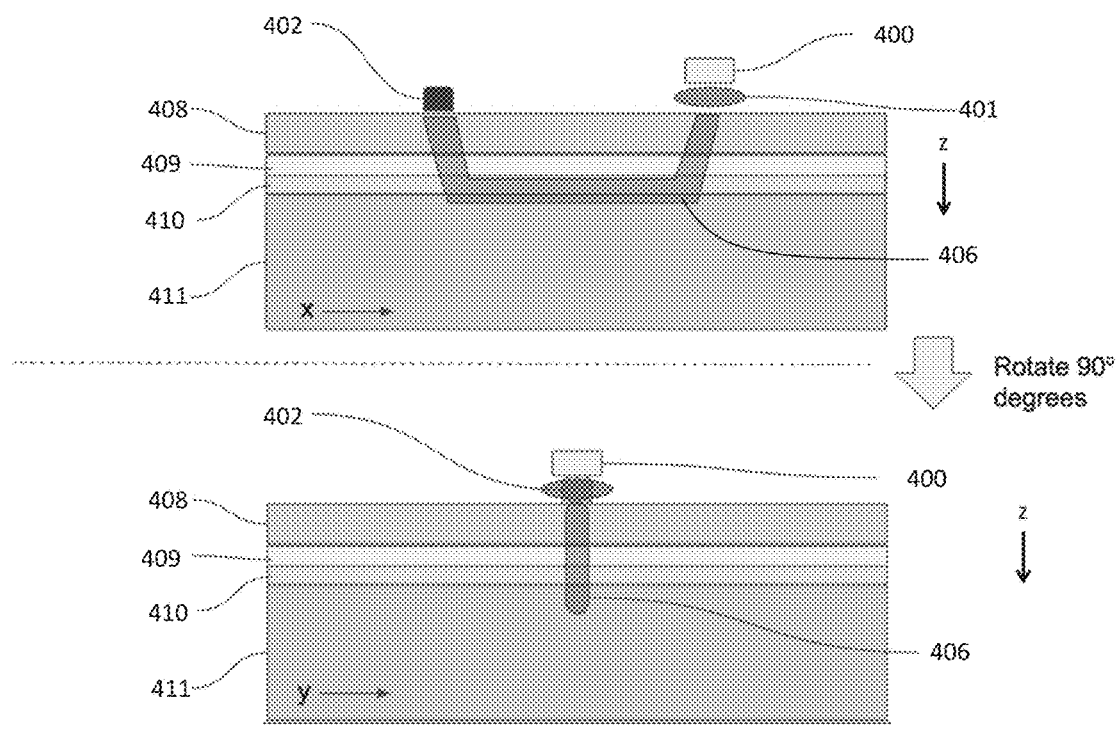
FIG. 4C depicts a cross-sectional view of the optical path(s) of FIG. 4B rotated 90 degrees.

FIG. 4C is a schematic cross-sectional view of a region of a patient's head and tissue underneath the scalp (408). A light source (402) and camera (400) and any optional associated optical components (401) may be placed against the scalp (408) to image regions of interest in the skull (409), cerebral spinal fluid (CSF, 410), and/or cortical brain tissue (411). Additional cameras and light sources may be used, as described above. One example of an optical path (406) between the light source (402) and the camera (400) is depicted, where a photon on that optical path may move along the Z-direction and across the XY plane. The reference path length may be selected based on the distance between the light source (402) and the camera (400) and the depth of the region of interest, and may, for example, be approximately (or greater than) the sum of the distance between the light source and the camera and twice the depth of region of interest. As depicted in the top frame of FIG. 4C, a photon from the light source (402) that is detected by the camera (400) may have an optical path through the tissue where the a greater distance of the path is across the XY plane as compared to the distance along the Z-direction (bottom frame of FIG. 4C). As such, the resolution of these path-length-selected paths along the XY plane may be higher than its resolution along the Z-direction. Moreover, the XY plane may be oriented in different directions for different light source locations and for different individual lock-in cameras. Thus, by rapidly moving the light source into different positions along the path (404) shown in FIG. 4A, within the timescale with which it is desired to perform a functional measurement of brain activity at several locations in parallel, the total set of measurements taken by all lock-in cameras as the light source moves may contain sufficient information to reconstruct a tomographic image or map of functional brain activity. Alternatively or additionally, the system may comprise a plurality of stationary light sources that are located such that they form a desired pattern. One or more of the plurality of stationary light sources may be activated in a desired sequence, which may simulate the effect of a single movable light source.

The one or more lock-in cameras may be arranged in any desirable pattern over a patient's head. For example, they may be arranged or located in a symmetric or asymmetric array, and/or may be arranged in a circular or radial pattern or a square-shaped or rectangular-shaped pattern. The field-of-view of the plurality of lock-in cameras may have areas of overlap and/or may have little or no overlap. In some variations, a plurality of lock-in cameras may be tiled adjacent to each other such that their individual fields-of-view are adjacent to each other with little or no overlap. The aggregate of the individual fields-of-view may simulate a single camera with a large field-of-view. The one or more lock-in cameras may be mounted on a patient's head at locations that correspond to the locations of the structures beneath the scalp that are to be imaged or monitored. Individual cameras may be attached to skin by one or more adhesives, straps, clips, and the like, which may be optionally coupled to a cap or hat, headband, helmet, and any type of head gear or apparel. Alternatively or additionally, one or more cameras and light sources may be disposed on a tip of a hand-held probe or wand. The tip of the wand may be placed against a patient's scalp at a region of interest and moved across the scalp to change the imaging area. The reference path length may be selected to image tissue at a particular depth of interest, and moving the hand-held probe or wand over the surface of the scalp may help to generate a map of the optical properties of the tissue at the depth of interest.

Light Playback System

Figure 3B:
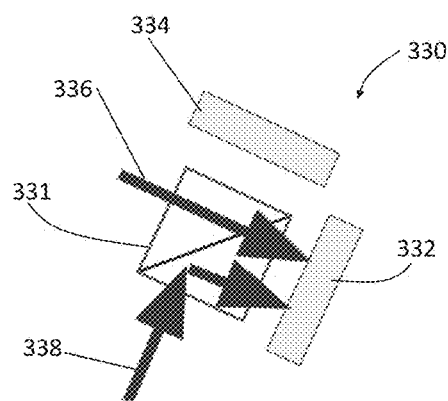
FIG. 3B is a schematic depiction of one variation of an optical assembly for low-coherence interferometry comprising a lock-in camera and spatial light modulator.

Optionally or alternatively, a low-coherence interferometry imaging system may comprise an optical assembly comprising a light source paired with a locked-in camera. Some variations the optical assembly may comprise a spatial light modulator located in the optical path of the light source. The spatial light modulator may receive light from the light source, alter a property of this light, and emit the altered light to the tissue sample (e.g., patient scalp). The light emitted by a spatial light modulator may have characteristics (e.g., phase and/or amplitude) that are based on the quasi-ballistic and/or ballistic photons detected by its corresponding lock-in camera. A spatial light modulator can comprise an array of amplitude and/or phase modulating pixels. A particular amplitude or phase modulation pattern detected by the camera may be displayed on the spatial light modulator to generate the phase conjugate (e.g., a digitally time-reversed wavefront with respect to the path-length-selected wavefront that has been measured on the camera). This configuration may help to amplify the proportion of quasi-ballistic photons that are present in the sample. The light source (and/or spatial light modulator) and its corresponding lock-in camera may be co-localized (i.e., light beam from the light source enters tissue in the same region from which the quasi-ballistic and/or ballistic photons are recorded). For example, the light source or emitter and/or spatial light modulator may be located between about 0.5 mm to about 2.5 cm apart from the lock-in camera and/or may be arranged such that the field-of-view of the camera is illuminated by the light source or emitter and/or spatial light modulator. Alternatively, the light source (e.g., spatial light modulator) may be adjacent to its corresponding lock-in camera or at another location on the scalp. FIG. 3B depicts a schematic depiction of one variation of an optical assembly (330) comprising a lock-in camera (332), a spatial light modulator (334, SLM) in communication with the lock-in camera (332), a light source or emitter that provides a light beam (336), and a combiner (331) that receives the light beam (336) and directs it to the lock-in camera (332). The combiner (331) may also be configured to direct light (e.g., from a patient's scalp, represented by arrow 338) to the lock-in camera (332), and/or direct light from the SLM (334) to a patient's scalp, and/or direct light from a light source to the SLM (334). The optical assembly (330) may comprise additional optical components, for example, such as one or more of the optical components of FIG. 3A. For example, the optical assembly (330) may comprise the optical components as arranged in FIG. 3A, but may comprise instead a SLM instead of mirror (303), where the SLM is in communication with a processor and/or the camera (310). Alternatively or additionally, a SLM may be provided in the same optical plane as mirror (309), and/or any location such that light emitted from the SLM can be directed to the tissue. The optical assembly (330) may also emit a low-coherence light to a patient's scalp or sample tissue, where the low-coherence light may be generated by a light source (such as any of the low-coherence light sources described above) and/or emitted from the SLM, which may provide light having a particular amplitude and/or phase as specified by data from the lock-in camera and/or processor. In some variations, the lock-in camera (332) may be aligned pixel-by-pixel with the SLM (334), which may extend the lock-in camera into a digital optical phase conjugation (DOPC) setup for amplified, selective playback of the path-length-selected photons. The DOPC setup may be configured to record, via lock-in camera quadrature measurement of amplitude and phase at each speckle grain, the coherence-gated (i.e., path-length-gated) wavefront resulting from ballistic and/or quasi-ballistic photons. The light source paired with that camera may be able to emit light (e.g., "play back" light) that is a phase conjugate copy (or equivalently a "time reversed" copy) of the wavefront. This phase-conjugate wavefront may retrace the aggregate optical paths back through the tissue, i.e., may retrace selectively the path-length-selected paths. This configuration may be used to increase the ratio of photons traveling along path-length-selected paths as compared with non-path-length-selected paths within the sample, as opposed to merely making the detection process more selective for any given proportion of path-length-selected paths over non-path-length selected paths. Some variations may comprise multiple optical assemblies that may each be located at various regions on a patient's scalp, which may allow phase-conjugated light to traverse laterally across a patient's skull.

Methods

Overview

The methods described herein may extend traditional OCT methods that generate images using ballistic photons by also utilizing quasi-ballistic photons. The full amplitude of the beat pattern generated by interference between a sample light beam and a reference light beam may be extracted and recorded using a lock-in camera, and may be used to calculate the number of ballistic and/or quasi-ballistic photons traveling between the light source and the camera that have a selected path length. The number of ballistic and/or quasi-ballistic photons (i.e., intensity or amplitude of such light) may be determined by measuring each of several phase-shifted interference patterns at each speckle grain with a lock-in camera and subsequent processing of the multiple values stored in the data bins of a lock-in camera to compute an estimate of this amplitude, and then averaging the resulting amplitude estimate across all pixels or speckle grains. These methods may select for ballistic and/or quasi-ballistic photons despite the spatial incoherence of the speckle patterns or phases. That is, these methods may perform a path-length-selective measurement by directly operating on imaged speckle patterns that result from light scattering diffusively over one or several centimeters in a dynamic scattering medium. This method may allow imaging of tissue structures in a large, highly scattering medium containing many scattering events at greater depths than traditional OCT methods and at greater spatial resolution than diffuse optical tomography methods.

In one variation of a method, a processor may calculate the absolute value of the difference ($|I_1-I_2|$) of two intensity values ($I_1$ and $I_2$) stored in two bins within each pixel of a lock-in camera, with the two intensity values corresponding to phase shifts of the reference beam by 0 or $\pi$ respectively. Alternatively, the camera may store four intensity values within each pixel, corresponding to phase shifts of the reference beam by 0, $\pi/2$, $\pi$ and $3\pi/2$, and the processor may calculate the quadrature amplitude using the formula Sqrt $[(I_2-I_4)^2+(I_1-I_3)^2]/2$ for each pixel, or other ways of computing the quadrature amplitude. The processor may then average the result of this pixel-specific computation (i.e., pixel value) over all pixels to compute an estimate of the amount of light passing between source and detector within the user-determined path-length range. e.g., in order to selectively measure the optical properties of the sample as probed by quasi-ballistic light paths. That is, for each pixel k, a pixel value may be $P_k=|I_1[k]-I_2[k]|$ for two-bin detector pixel or a pixel value may be $P_k=\text{Sqrt}[(I_2[k]-I_4[k])^2+(I_1[k]-I_3[k])^2]/2$ for a four-bin detector pixel and then take the average over all N pixels $(1/N)*\Sigma_{k=1 \text{ to } k=(N)} (P_k)$ as the output indicative of the number of path-length-selected photons passing between the source and detector.) This method may be used to selectively measure an optical property, e.g., an activity-dependent optical property, of a target voxel or region within the brain tissue as probed by quasi-ballistic photon or otherwise path-length selected paths, while ignoring the effects of non-path-length-selected paths, thus improving the spatial resolution of the measurement of the optical property as compared with diffuse optical tomography.

Figure 5A:
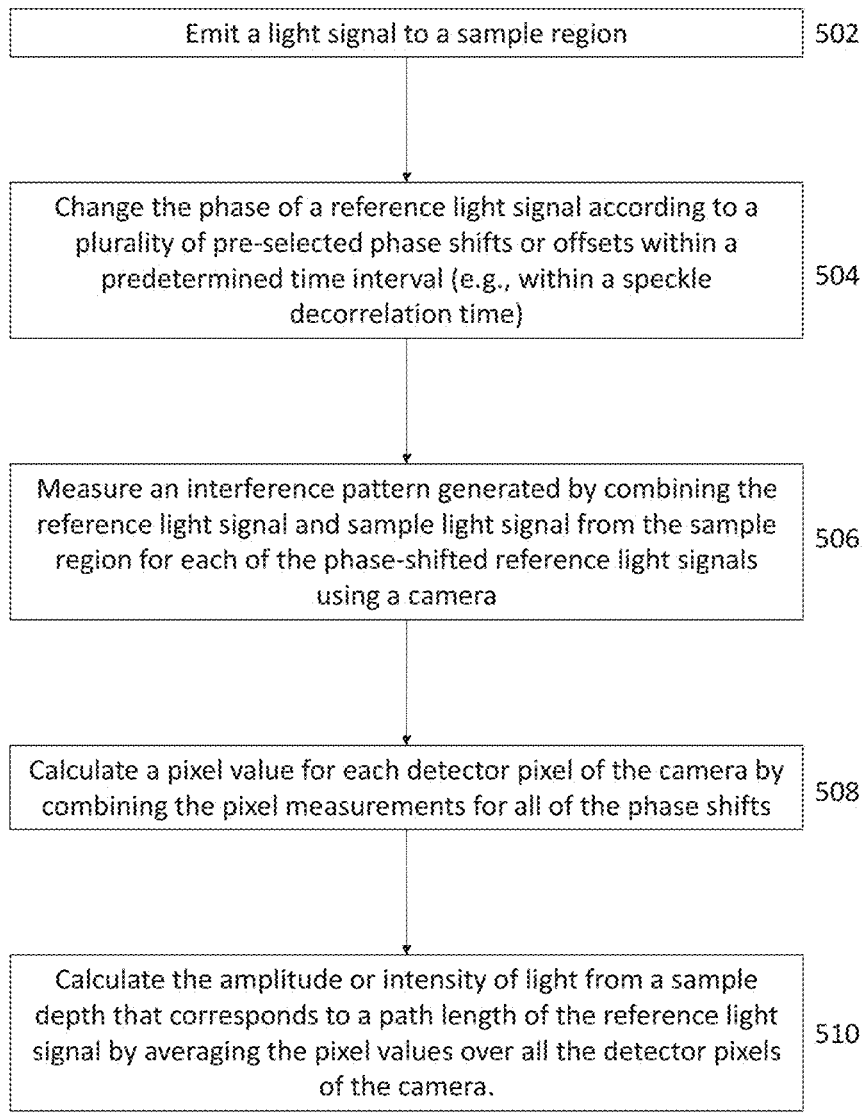
FIG. 5A depicts one variation of a method of low-coherence interferometry for non-invasive brain imaging.

FIG. 5A depicts one variation of a method (500) of low-coherence interferometry for non-invasive brain imaging. The method (500) comprises emitting (502) a light beam or signal to a sample region, such as a brain region of interest, changing the phase of a reference light signal (504) according to a plurality of pre-selected phase shifts or offsets within a predetermined time interval (e.g., with the speckle decorrelation time of the desired imaging depth below the sample surface), measuring (506) the interference pattern for each phase-shifted reference light signal, computing (508) pixel-specific outputs using the multiple values stored in the multiple bins of each pixels, and then averaging or summing (510) those pixel-specific computed outputs over the array of pixels of the lock-in camera to obtain a high signal-to-noise ratio estimate of the number of photons traveling along path-length-selected paths between source and detector. The light beam may be generated by any of the low-coherence light sources described above. In some variations, the phase shifts or offsets may be introduced by changing the path length of the reference light signal. For example, a set of pre-selected phase shifts may comprise two phase shifts of π (e.g., 0, π), or may comprise fourth phase shifts of π/2 (e.g., 0, π/2, π, 3η/2). The reference light signal may be stepped through the set of pre-selected phase shifts or offsets within a predetermined time interval, for example, in about 1 ms or less (e.g., from about 500 to about 2 ms, e.g., about 800 μs, about 1 ms, about 2 ms, etc.), and/or shorter than the speckle decorrelation time. Combining the phase-shifted reference light signals with the sample light signal may generate an interference pattern for each phase shift. The measurement of the interference pattern may be performed by a lock-in camera. In some variations, the light interference pattern detected by the camera may be represented by a speckle pattern. The camera may output speckle pattern data or measurements, where the output of each camera detector pixel corresponds to a grain of the speckle pattern. In some variations, the size of the detector pixel may be matched via a magnification system to the size of the speckle grain, as described above. Each interference pattern for each phase-shifted reference light signal may be represented by its own speckle pattern measurement. The method may comprise calculating a combined pixel value for each pixel by adding the multiple values stored within each pixel (e.g., computing the absolute value of the difference across two data bins of a pixel, or computing the quadrature amplitude using four data bins of a pixel). This may reduce or eliminate the contribution of non-path-length-selected photons while preserving the interference terms associated with path-length-selected photons (e.g., ballistic or quasi-ballistic photons). By combining such stored interference measurements, each at a different phase, from within each pixel, a pixel value may be calculated for each pixel that depends only on those photons which have traveled along the path-length-selected paths, with other interference terms being reduced or canceled out of the computation. The calculated pixel value may represent an estimate of the total number of photons which have passed between the low-coherence light source and lock-in camera's field of view (which may be about 1 mm in size or less) along path-length-selected paths. For example, for a 2-bin lock-in camera, the quantity computed using the two bin measurements stored at the kth pixel may be $P_k=|I_1[k]-I_2[k]|$ where |x| denotes the absolute value of x. For a 2-bin lock-in camera, the measurements at each pixel contain a multiplicative term that depends on an unknown, speckle-grain-specific phase, and thus the results of the computation at any given pixel does not uniquely determine the number of path-length-selected photons traveling between source and detector. However, by averaging the outputs of these pixel-specific computations over all pixels, the effect of the unknown phase at each pixel may be reduced or eliminated, using quadrature detection, e.g., according to the formula $P_k=\text{Sqrt}[(I_2[k]-I_4[k])^2+(I_1[k]-I_3[k])^2]/2$. For both 2-bin and 4-bin variations, however, the $P_k$ values are subject to low signal-to-noise ratios with respect to photon shot noise in the reference beam as well as in the light emerging from the sample, and thus averaging over all pixels of the lock-in camera may help to obtain a more precise and high signal-to-noise ratio estimate of the number of path-length-selected photons traveling between source and detector. Thus, the storage by the lock-in camera of four phase-shifted interference values within each pixel, combined with the ability to perform computations on those stored values, and further combined with the ability to average the outputs of these pixel-specific or within-pixel computations over all pixels of the camera, enables precise estimation of the number of path-length-selected photons traveling between source and detector, e.g., between a ~1 mm light source at one location on the scalp and the ~1 mm or lower field of view of the lock-in camera on the scalp. Optionally, the method (500) may be combined with phase conjugation methods to selectively amplify the wavefront of ballistic, quasi-ballistic, and/or other path-selected photons, thus increasing the relative proportion of such path-length-selected paths traveling within the sample on the subsequent iteration of the measurement. Some methods may optionally comprise polarizing the reference light signal and the light signal that is emitted to the sample region, and then filtering the resultant interference pattern based on the polarization orientation to further select for ballistic and/or quasi-ballistic photons.

Although not wishing to be bound to any theory or basis, it is believed that methods that comprise cycling the reference light beam through a plurality of pre-set shifts or offsets may help select for quasi-ballistic photons from a tissue structure or voxel of interest over background scatter photons and/or photons from surrounding structures by generating multiple measured intensity values at each pixel, each stored in a separate bin of the lock-in camera, computing functions of those multiple measured intensity values stored at each bin of each pixel of the lock-in camera, with such functions removing background terms corresponding to non-path-length-selected light and also optionally removing the effects of random speckle-specific phase offsets. Averaging the intensity values of each detector pixel of the detector array for each speckle pattern that corresponds to each of the pre-selected shifts or offsets may help to increase the signal to noise ratio of the measurement and/or further remove the effects of the random speckle-specific phase offsets, resulting in a high signal to noise ratio estimate of the number of photons passing between source and detector along path-length-selected paths. These methods may help improve the spatial resolution and sensitivity of anatomical, vascular and/or functional brain imaging and/or brain computer interfacing.

Varying the Reference Light Beam or Signal

In one variation, changing a reference light signal to have a phase-shift or offset may comprise inserting a phase modulator into the reference beam path. Alternatively or additionally, a phase-shift or offset may be introduced into the reference light signal by adjusting the path length of the reference beam. For example, turning to FIG. 3A, the reference path length may be adjusted by moving the mirror (318) relative to the beam splitter (316). The interference pattern detected by the lock-in camera may be represented by a speckle pattern. The camera may output speckle pattern data or measurements, where each camera detector pixel maps to a grain in the speckle pattern. The number and value/size of phase shifts or offsets may be pre-selected, for example, based on the type of lock-in camera that is used. A system comprising a quadrature-demodulating lock-in camera may comprise a method where the reference light signal is cycled through four pre-selected phase shifts or offsets. This may correspond to measuring four quadrature phases, which may be attained by adjusting the reference path length by phase increments of $\pi/2$, while remaining within the regime for selecting sample photons having a path length that approximates the reference path length via OCT coherence gating. Alternatively, a system may comprise a lock-in camera comprising pixels having two data bins, and methods may comprise cycling the reference light beam through two pre-selected phase shifts or offsets (e.g., in increments of $\pi$). This succession of multiple measurements at multiple defined phase offsets may be done quickly, i.e., within a pre-determined time interval within the speckle decorrelation time of the speckle pattern. If it is not done within the speckle decorrelation time, then the random phase offset and/or background will change in between the successive measurements, which may corrupt the measurement such that the calculation of the intensity or amplitude of the quasi-ballistic photon fraction is no longer possible and/or accurate.

In one variation and with reference to FIG. 3A, changing the phase or offset of a reference light beam may comprise adjusting the path length difference between the reference beam path and the sample beam path (corresponding to reflections from the selected depth d) so that $\Delta z\ll$coherence length of light source (which could be ~100 µm), i.e., signal from depth d and reference arm path lengths are approximately equal to with $\Delta z$. For example, for a 4-bin quadrature-demodulating lock-in camera, the reference path length may be varied successively on each of four successive measurements to $k\Delta z=0$, $\pi/2$, $\pi$ and $3\pi/2$ (or two successive measurements for a 2-bin lock-in camera for $k\Delta z=0$, $\pi$). The number of pre-selected phase shifts or offsets and number of data bins per pixel may vary. The pre-selected phase shifts or offsets differ from each other by the same interval (e.g., all spaced apart by $\pi$ or $\pi/3$, or $\pi/2$, etc.) or may have different intervals. A detector pixel may comprise any number of data bins per detector pixel, for example, 2, 3, 4, 5, 6, 7, 8, 10, 12, 14, 16, 18, 20, 25, 32, 36, etc.

Alternatively or additionally, a set or series of pre-selected phase shifts or offsets used to measure the amplitude of the interference (or beat) pattern on the lock-in camera may be obtained by the use of a phase shifter, such as an electro-optic modulator, and/or acousto-optic modulator, inserted in the reference beam path. Some variations may comprise a plurality of reference light beams which each have a fixed phase plate that implements a phase shift, and a multiplexor that selects between the light beams. Some methods may option ally shift the wavelength of the reference light beam to generate interference patterns with certain wavelength(s) of light from the sample.

Measuring Interference Patterns and Calculating Quasi-Ballistic Photon Intensity or Amplitude In one variation, a method may comprise detecting the interference patterns resulting from combining reference light beams with n number of different pre-selected phases p with the sample light beam using a lock-in camera to generate a corresponding speckle pattern measurement $SP_p$. The lock-in camera may comprise an array of detector pixels, where each detector pixel has one or more data bins. The number of pixel data bins may correspond to the number of pre-selected phase shifts of offsets. The measured speckle pattern $SP_p$ corresponding to each phase shift p may be stored in data bin $B_p$ of each pixel in the array. A computation represented by a mathematical function F may be performed on the n different values $B_p$ for p=1, 2, ..., n stored in the different bins within each pixel, represented as $F(B_p[k]$ for p=1, 2, ..., n), where k denotes the kth pixel on the lock-in camera. For example for a 2-bin scheme above, $F(B_p[k]$ for p=1, 2, ..., n)=$|B_1[k]-B_2[k]|$ or alternatively $F(B_p[k]$ for p=1, 2, ..., n)=$(B_1[k]-B_2[k])^2$. The results of these functions may be summed over all m pixels in the array, i.e., $\Sigma_k F(B_p[k]$ for p=1, 2, ..., n). Optionally, an average intensity value may be calculated by dividing the sum by the number of pixels m in the array resulting in the Sum from k=1 to k=m of $F(DB_p[k]$ for p=1, 2, ..., n) as an estimate of the number path-length-selected photons passing between the source and the detector.

The contribution of quasi-ballistic and/or ballistic photons to an interference pattern or speckle pattern may be the sum of all the pixel computation $F(B_p[k]$ for p=1, 2, ..., n) or may be the average of all the pixel computations $F(B_p[k]$ for p=1, 2, ..., n).

Figure 5B:
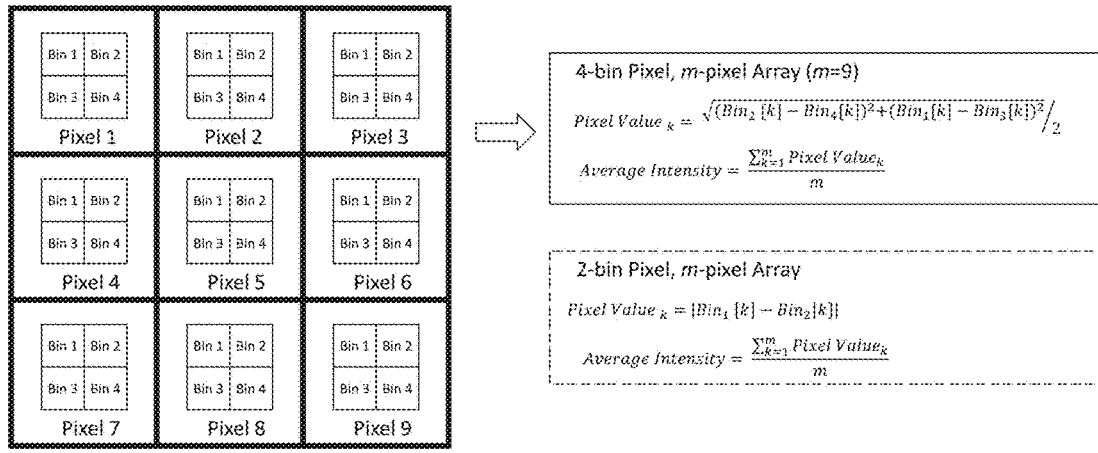
FIG. 5B is a schematic depiction of one variation of a method of low-coherence interferometry for non-invasive brain imaging.
Figure 5C:
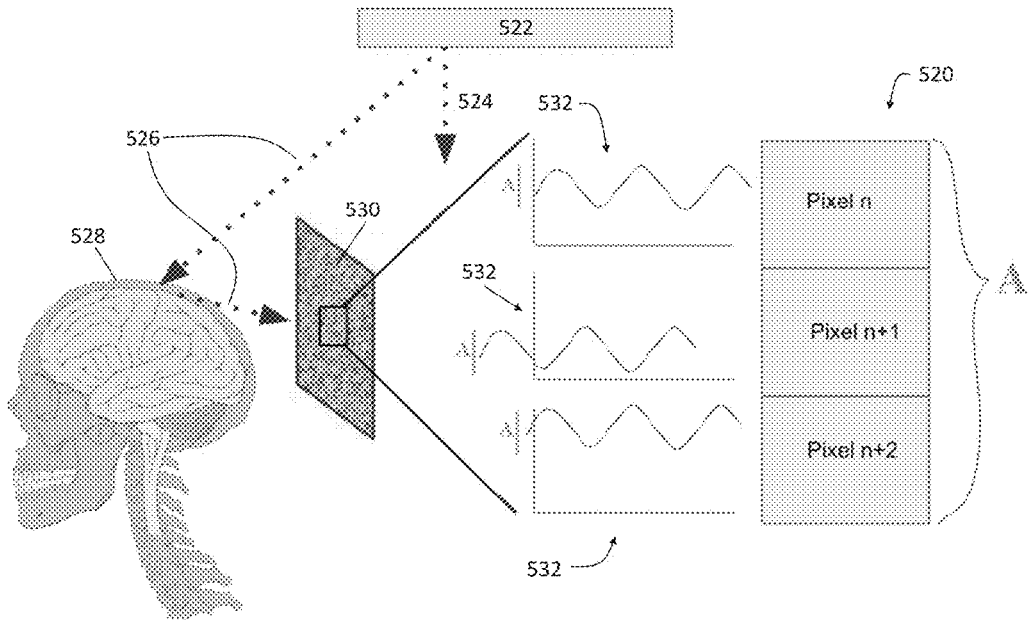
FIG. 5C depicts one example of an application of low-coherence interferometry imaging methods to image blood oxygenation changes in brain tissue.

An illustrative example of this method is schematically depicted in FIG. 5B. In this example, the lock-in camera has a 3×3 array of detector pixels (pixels 1-9, m=9), where each pixel has four data bins (data bins 1-4, n=4), and the number of pre-determined phase shifts or offsets is four (offsets 1-4). A first inference pattern resulting from a phase shift or offset number 1 may be stored in data bin 1 for all nine detector pixels, which may be represented as a first speckle pattern measurement. The quadrature amplitude or pixel value for each pixel $F(B_p[k]$ for p=1, 2, ..., n)=$Sqrt[(B_2[k]-B_4[k])^2+(B_1[k]-B_3[k])^2]/2$ for each pixel k may be calculated, and the average intensity over the entire array of detector pixels may be calculated by averaging the pixel values over all m pixels $(1/m)*\Sigma_{k=1\ to\ k=m} F(B_p[k]$ for p=1, 2, ..., n). In the case of a lock-in camera comprising an m-pixel array where each pixel has two bins, the pixel value may be $F(B_p[k]$ for p=1, 2, ..., n)=$|B_1[k]-B_2[k]|$, and average intensity over the entire array of detector pixels may be calculated by averaging the pixel values over all m pixels $(1/m)*\Sigma_{k=1\ to\ k=m} F(B_p[k]$ for p=1, 2, n).

For example, in methods that comprise cycling the reference light beam through four pre-selected phase shifts or offsets (in a pre-determined time interval of about 1 ms or less), the amplitude of quasi-ballistic light from the sample (e.g., brain tissue) that has contributed to the interference pattern may be calculated using, for example, quadrature detection. Although quasi-ballistic photon intensity or amplitude is calculated based on four pre-selected shifts or offsets, it should be understood that similar methods may be performed based on two, three, five or more pre-selected shifts or offsets. To further explicate the principles of quadrature detection, if there are four measured signals ($I_1$, $I_2$, $I_3$, $I_4$) of the form $A+B \times Cos(\varphi_{control}+\varphi_{unknown})$ with $\varphi_{control}$ being set to 0, $\pi/2$, $\pi$ and $3\pi/2$, then both the amplitude B and the unknown phase $\varphi_{unknown}$ may be extracted by solving the resulting four equations and using standard trigonometric identities, resulting in $A \sim I_1, I_2+I_3+I_4$, $B \sim Sqrt[(I_2[k]-I_4[k])^2+(I_1[k]-I_3[k])^2]/2$ and $\varphi_{unknown} \sim ArcTan[(I_4[k]-I_2[k])/(I_1[k]-I_3[k])]$. Here, the phase offsets correspond to offsets in a slow beat envelope intensity pattern formed by optical interference. This results from the random speckle grain phase interfering with a common reference beam phase, with the optical phase difference—corresponding to only nanometers in the visible or near-infrared domains—being transferred to an equivalent angular phase difference in the resulting beat envelope pattern.

In one variation and with reference to FIG. 3A, the power at a camera detector pixel with coordinates (x,y) may be:

$P_{background}$(non-selected path lengths)+$P_{signal}$(selected path length)$P_{reference}$(matches selected path length)+$2(P_{signal} P_{reference})^{1/2} \cos(k\Delta z + \varphi_{unknown})$(interference terms that vanish because their path length difference>>coherence length of light source)

$P_{background}, P_{signal}, P_{reference}$ may be constant across all four reference path length adjustments $\Delta z_1, \Delta z_2, \Delta z_3, \Delta z_4$ which can be ensured by making all four phase-shifted measurements within the speckle decorrelation time. The method may comprise extracting the size of the quantity $P_{signal} \times P_{reference}$ by adjusting the reference arm successively on each of four successive measurements to $k\Delta z=0, \pi/2, \pi$ and $3\pi/2$ (or two successive measurements for a 2-bin lock-in camera for $k\Delta z=0, \pi$)

Even though $\varphi_{unknown}$ is an unknown and random phase, specific to each pixel, which results from the laser speckle pattern due to light scattering in the tissue, by measuring and storing each of these four measurements at different values of $k\Delta z$, the value $2(P_{signal} P_{reference})^{1/2}$ may be extracted via quadrature detection. The camera output may then be average of this value over many detector (or all) pixels in the camera to average out noise sources, e.g., shot noise in the reference beam, and improve the signal to noise ratio.

Having extracted the term $2(P_{signal} P_{reference})^{1/2}$, the method may further comprise computing the quantity of interest, $P_{signal}$, which represents a quantity proportional to the number of detected quasi-ballistic photons, selected on the basis of their path length, since the reference beam power is known (e.g., may be stored in a processor memory).

FIG. 5C depicts one example of an application of low-coherence interferometry imaging methods to image blood oxygenation changes in brain tissue (e.g., in the context of through-skull, three-dimensionally resolved imaging of anatomical, functional or vascular activity in the human brain). In this method, a camera (520) is positioned along a patient's head (528) at a distance away from a light source (522). The camera (520) may be a lock-in camera and the light source (522) may be a low-coherence light source. A sample beam path (526) and a reference beam path (524) are combined to form an interference pattern, which may be represented as a speckle pattern (530). The temporal beat patterns (532) formed by the interference between the sample beam path (526) and the reference beam path (524) may each be detected and stored in a pixel of the camera (520). Three beat patterns and three corresponding pixels are depicted for the sake of clarity. The amplitude (A) of each of these beat patterns may be averaged together to generate an average intensity value that represents the number of quasi-ballistic and/or ballistic photons as selected by the path length of the reference light beam. The amplitude (A) of each of the beat patterns may be the same, or may be different from each other. Averaging the amplitude (A) over all the pixels (n, n+1, n+2) may help to eliminate random phase offsets, random baseline offsets, and/or noise from the intensity measurement. These methods may be used to measure optical absorption changes, for instance corresponding to neural activity dependent blood oxygenation changes (e.g., amount of oxygenated or deoxygenated hemoglobin) in the human brain.

Figures 6A, 6B:
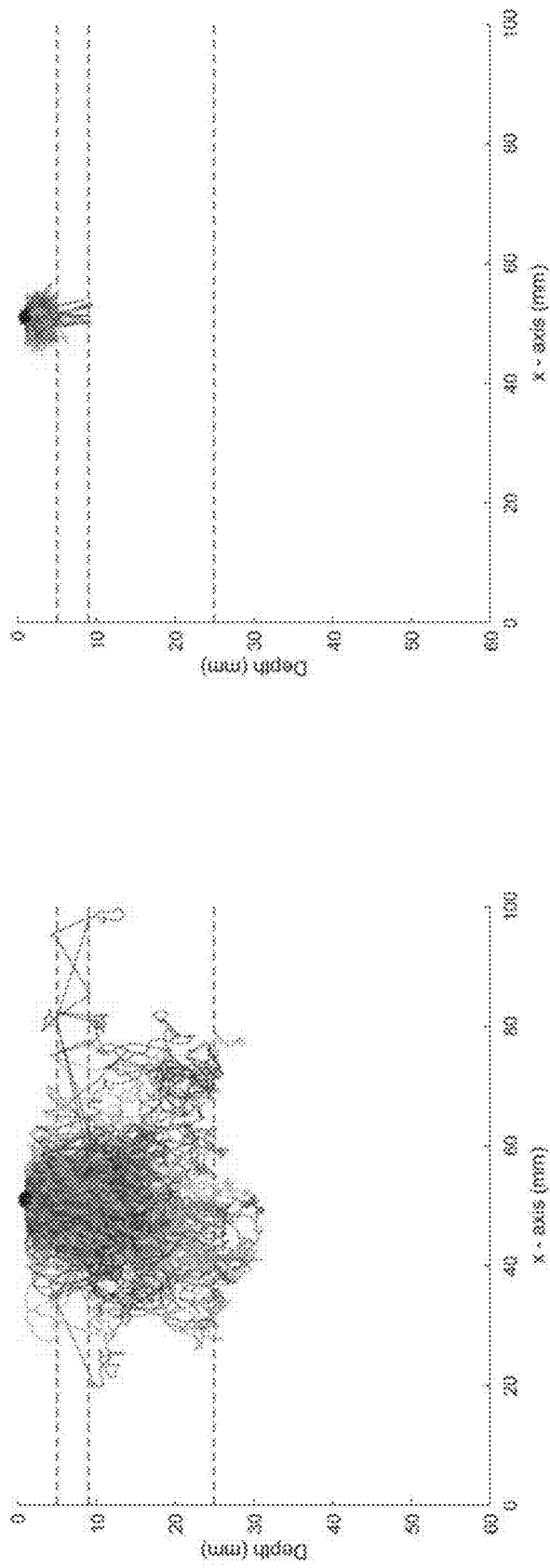
FIGS. 6A-6B depict the spatial resolution of low-coherence interferometry images based on a simulation of photon paths in a model of the human skull and brain.

A simulation of the spatial resolution improvement, based on Monte Carlo modeling of photon paths in the human skull and brain using the software Monte Carlo eXtreme is shown in FIGS. 6A-6B. The simulation was performed for 1 mm² light emitters and detectors (e.g., a field of view of the lock-in camera imager), through 4 mm of skull and 4 mm of cerebrospinal fluid, with brain underneath, and demonstrates that the methods described herein are able to select for photons (e.g., quasi-ballistic and/or ballistic) that correspond to a desired imaging depth of about 10 mm, while rejecting photons from other tissue regions and background scatter. In this figure, the light emitters (or light sources) and detectors are located adjacent to each other, at approximately the same area on the scalp, with little or no lateral distance between the emitters and detectors (e.g., may be arranged similarly to the light sources and detectors in FIG. 1A). FIG. 6A depicts representative paths of photons reaching the detector. FIG. 6B depicts only photons with the selected path length range. Photons with path lengths between 16 mm and 20 mm were selected. As depicted in FIG. 6B, the spatial spread of photons along the paths selected by OCT is greatly reduced compared to those in FIG. 6A without OCT, corresponding to an increase in the spatial resolution of any measurements of tissue optical properties being performed using photons which travel along these selected paths. To further discriminate against photons with larger numbers of scattering events along their path compared to quasi-ballistic photons, the system may further comprise a polarization-selective filter. While polarization orientation eventually randomizes in scattering media, it may be partially preserved for the first few scattering events and preferentially so for forward-scatter, leading to an additional selection mechanism for photons which have undergone only a small number of predominantly forward-scattering events, i.e., quasi-ballistic photons. For example, polarization-selective filtering may be achieved by circularly polarizing the reference light beam and the light beam that is emitted to the sample, with interference only occurring efficiently among photons that maintain this same circular polarization.

Optionally, some methods may comprise selecting photons based on their exit angle from the sample (and/or angle of incidence on the detector array). For example, light that meanders approximately straight down into the tissue and straight up from the tissue may emerge from the tissue with a relatively narrow angular cone. Such photons may be represented in a speckle pattern with large speckle spots. In one variations, a spatial Fourier transform of a gated speckle pattern may generate a profile of the angular scattering distribution, and may preferentially weigh the low-spatial frequency components to select for the light that associated with low-angle scatter (i.e., light that meanders approximately straight down and straight up).

Phase Conjugation to Amplify Quasi-Ballistic Photons

Figure 7A:
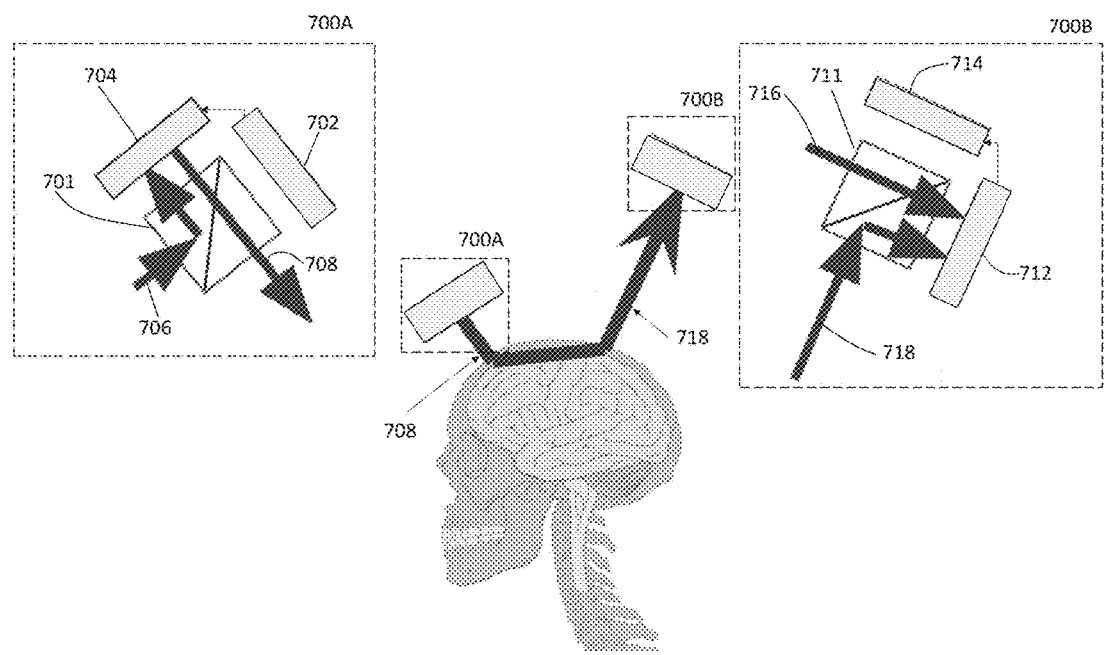
FIG. 7A depicts one variation of a low-coherence interferometry imaging system.

Optionally, a method may comprise amplifying the proportion of quasi-ballistic photons that are present in the tissue sample. In one variation, a system may comprise a DOPC optical assembly as described previously, which may comprise a lock-in camera aligned with sub-pixel-level accuracy to a spatial light modulator. FIG. 7A depicts one variation of a system comprising a first optical assembly (700A) and a second optical assembly (700B). The first optical assembly (700A) may comprise a lock-in camera (702), a SLM (704) in communication with the lock-in camera (702), a light source or emitter that provides a light beam (706), and a combiner (701) that receives the light beam (706) and directs it to the SLM (704). The combiner (701) may also be configured to direct light (e.g., from a patient's scalp) to the lock-in camera (702), and/or direct light from the SLM to a patient's scalp (represented by arrow 708). The second optical assembly (700B) may comprise a lock-in camera (712), a SLM (714) in communication with the lock-in camera (712), a light source or emitter that provides a light beam (716), and a combiner (711) that receives the light beam (716) and directs it to the SLM (714). The combiner (711) may also be configured to direct light (e.g., from a patient's scalp, represented by arrows 718) to the lock-in camera (712), and/or direct light from the SLM to a patient's scalp. While the first optical assembly (700A) is depicted as emitting light from the SLM (704) (e.g., in a light playback mode) and the second optical assembly (700B) is depicted as receiving or measuring light from the tissue sample or scalp (e.g., in a measurement mode), it should be understood that the first optical assembly (700A) may be receiving or measuring light from the tissue sample or scalp (e.g., in a measurement mode), and the second optical assembly (700B) may be emitting light from the SLM (714) (e.g., in a light playback mode). The first optical assembly (700A) may be spaced apart at a distance from the second optical assembly (700B), e.g., about a few millimeters to many centimeters apart (e.g., about 0.5 cm to about 15 cm apart).

Figure 7B:
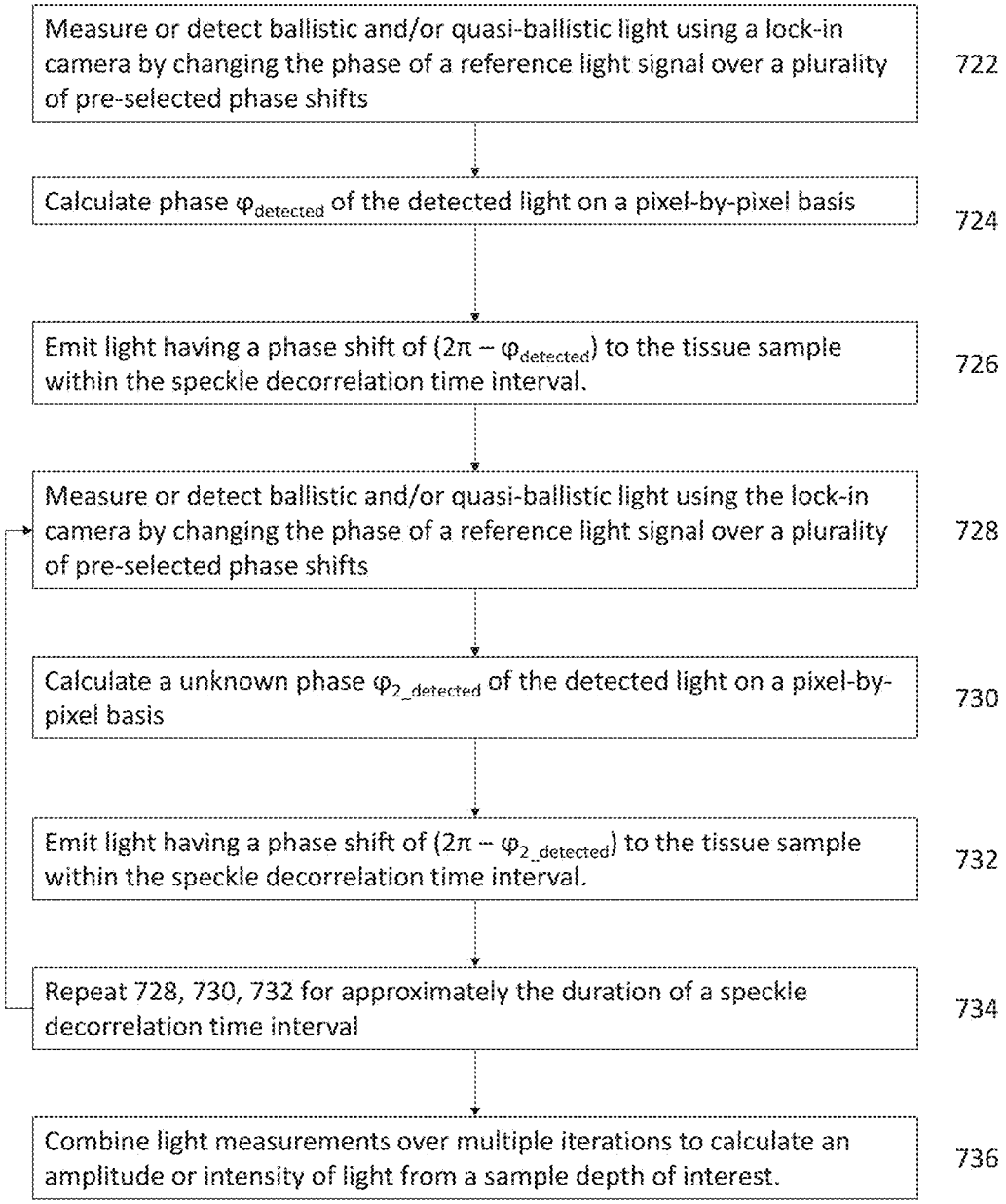
FIGS. 7B-7E depict variations of methods for amplifying the proportion of quasi-ballistic or otherwise path-length-selected photons by phase conjugation (e.g., using the system depicted in FIG. 7A).
Figures 7C, 7D, 7E:
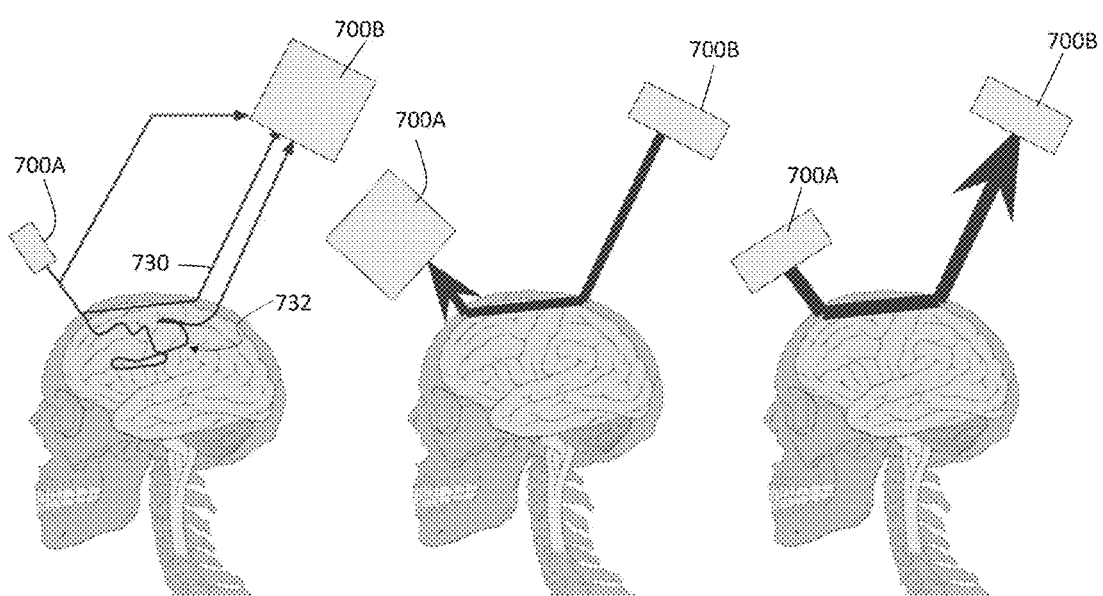

FIG. 7B depicts one variation of a method for amplifying the proportion of quasi-ballistic photons by phase conjugation, and FIGS. 7C-7E depict various steps of the method of FIG. 7B. Method (720) may comprise measuring or detecting (722) ballistic and/or quasi-ballistic light using a lock-in camera, calculating (724) a phase of the detected ballistic and/or quasi-ballistic light $\varphi_{detected}$ at each pixel (or speckle of a speckle pattern), emitting (726) light having a phase shift of $(\lambda\pi-\varphi_{detected})$ at each corresponding emitter pixel to the tissue sample (e.g., scalp) within a pre-selected time interval (e.g., within the speckle decorrelation time interval), measuring or detecting (728) ballistic and/or quasi-ballistic light using the lock-in camera, calculating (730) a second phase of the detected ballistic and/or quasi-ballistic light $\varphi_{2\_detected}$ at each pixel (or speckle of a speckle pattern), emitting (732) light having a phase shift of $(2\pi-\varphi_{2\_detected})$ at each pixel to the tissue sample within the pre-selected time interval (e.g., within the speckle decorrelation time interval), and repeating (734) the measuring, calculating and emitting steps (728), (730), and (732) for the duration of the pre-selected time interval (e.g., within the speckle decorrelation time interval). These steps may be repeated once, or may be repeated or iterated two or more times (e.g., about 2-15 times, about 5-10 times, about 10-12 times, about 10-15 times, about 3 times, about 4 times, about 5 times, etc.). The method (720) may further comprise combining (736) light measurements (e.g., ballistic and/or quasi-ballistic light measurements) over multiple iterations to calculating an amplitude or intensity of light from a sample depth of interest (and/or selected path length range of interest, and/or voxel of interest). Alternatively or additionally, some variations may comprise measuring a discretization of the phase and emitting light based on the discretization of the phase, and/or emitting light having a corresponding amplitude, and/or any other methods of optical phase conjugation. Phase conjugated light may be generated using a flat wavefront light source and a spatial light modulator (SLM). The phase shift of $(2\pi-\varphi_{2\_detected})$ at each pixel may be transmitted to the SLM, and used to adjust the SLM settings to modify light to have that phase shift at each pixel. Light from the flat wavefront light source may be provided to the SLM, which then introduces the phase shift of $(2\pi-\varphi_{2\_detected})$ at each pixel and then the phase-shifted light is directed to the tissue sample. The method (720) may be performed by a single optical assembly, where the optical assembly may switch between light measurement mode and light playback mode. Alternatively or additionally, the method (720) may be performed by two or more optical assemblies located at a lateral distance apart from each other, as depicted in FIGS. 7A and 7C-7E.

As depicted in FIG. 7C, the full wavefront of the path-length-selected photons (730) may be selectively measured over the scattered photons (732). The processor may compute a phase conjugate amplitude and/or phase pattern for display on a spatial light modulator. For example, an optical assembly such as the second optical assembly (700B) may measure or detect ballistic and/or quasi-ballistic light (i.e., detect coherence-gated light) using the lock-in camera (712). A reference light beam (716) may be generated by a first light source and cycled through a plurality of pre-selected phase shifts or offsets as described above, and combined with light from the tissue sample or scalp (718) using a combiner (716) to form an interference pattern on the camera (712). The camera may be a lock-in camera that is able to record the different interference patterns and generate a series of speckle pattern measurements or data for each of the phase shifts or offsets, as described above. The method may then comprise calculating amplitude and phase at each speckle grain to obtain the resultant coherence-gated (i.e., path-length-gated) wavefront. For example, the amplitude and phase $\varphi_{detected}$ of the detected light (which was previously referred to as $\varphi_{unknown}$) may be calculated, on a pixel-by-pixel (or speckle-by-speckle) basis, using quadrature measurement techniques described above, where $$\varphi_{detected}=\text{ArcTan}[(I_3[k]-I_2[k])/(I_1[k]-I_3[k])]$$

The calculated phase of the detected light $\varphi_{detected}$ may be transmitted to the SLM (714) to emit a "playback" light that is a phase conjugate copy of the wavefront within the speckle decorrelation time. The playback light may have a phase of $(\lambda\pi-\varphi_{detected})$ and may be generated using a spatial light modulator that is paired with the lock-in camera. A spatial light modulator may be any optical device is configured to modulate amplitude, phase, or polarization of light waves in in a spatially-varying manner. The spatial light modulator may be a phase modulator, and amplitude modulator or a phase and amplitude modulator, e.g., a liquid crystal modulator, digital micro-mirror device, or other form of spatial light modulator. Illuminating the spatial light modulator using a flat wavefront light source produces a phase-conjugated copy of the path-length-selected wavefront, so as to generate additional path-length-selected photons. This may result in an increased yield of path-length-selected photons. In turn, this increased number of path-length-selected photons may be used to probe or interrogate tissue structures at a tissue depth or location, or along specific paths within tissue, such that the path length corresponds to the reference path length. As depicted in FIG. 7D, this phase-conjugate wavefront may, with a certain degree of efficiency, retrace the aggregate optical paths back through the sample. The wavefront from the second light source may be detected by a second lock-in camera (e.g., the lock-in camera (702) of optical assembly (700A)), which may be paired with its own light source and SLM (e.g., SLM (704)). The amplitude and phase $\varphi_{2\_detected}$ of the detected light may be calculated on a pixel-by-pixel basis using quadrature measurement techniques as described above. The calculated phase of the detected light $\varphi_{2\_etected}$ may be transmitted to the SLM (704) to emit a "playback" light that is a phase conjugate copy of the wavefront within the speckle decorrelation time. The playback light may have a phase of ($2\pi-\varphi_{detected}$). As represented in FIG. 7E, an increased number of path-length-selected photons from the optical assembly (700A) may be detected by the optical assembly (700B), which may in turn be used to measure the full wavefront of the path-length-selected photons, and the processor may compute a phase conjugate amplitude and/or phase pattern for display on the SLM of the optical assembly (700B), which may produce a phase-conjugated copy of the path-length-selected wavefront, so as to generate further additional path-length-selected photons. This process may be iteratively repeated to progressively increase the number of path-length-selected photons on each back-and-forth pass between a first optical assembly and a second optical assembly.

The aggregate optical paths through the brain tissue may comprise the set of all optical paths or light field that are positively selected by coherence gating by the DOPC optical assemblies. The improvement in the proportion of the light field that can travel back along the aggregate optical paths, i.e., along quasi-ballistic paths, may be determined at least in part by the number of optical modes (i.e., optical degrees of freedom) of the DOPC setup (N) divided by the number of optical modes associated with the aggregate optical paths (M). As a rough approximation, M may be based on taking the smallest cross-section of the aggregate optical paths and dividing that by the speckle size (equal to (optical wavelength)/2 if speckles are fully developed). This estimate is a lower bound estimate that is accurate in the asymptotic limit where scattering coefficient goes to 0. A more direct determination of the improvement factor can be made by performing simulations with the specified N value and determining the improvement factor from the simulation.

The method may comprise iteratively repeating the phase conjugation process between the first light source and second light source, where the prior phase conjugate wavefront as detected by the lock-in camera that corresponds with each light source may serve as the input light field. This may facilitate the aggregation of optical paths toward a tuned set of optical paths that produce a stronger (or more intense) signal from quasi-ballistic photons. For example, if $N_0$ path-length-selected photons are detected on the first cycle and the system is in a regime of <1 path length selected photon per lock-in camera pixel, then after K iterations of phase conjugation, the number of photons within the path-length-selection range becomes:

$$N_k = N_0((N_0/M)^{K+1} - 1)/((N_0/M) - 1).$$

Note that all K of these iterations of phase conjugation preferably take place within the speckle decorrelation time (e.g., switching of the spatial light modulator across multiple pre-set offsets or shifts in less than about 100 microseconds for noninvasive operation through the human skull and into human brain tissue). If the iterations are spread over more than one speckle decorrelation time, then $N_k$ would be lower than the value in the expression. However, if $N_k > N_0$, the process would still yield an improvement. This procedure can lead to improved resolution in the measurement process by increasing the number of photons traveling along quasi-ballistic photon optical paths, and increasing their proportion relative to non-ballistic paths.

The invention claimed is:

1. A non-invasive system for measuring an activity-dependent optical property of a brain tissue region, the system comprising:
   a reference optical path having an adjustable path length between a lower bound and an upper bound, wherein the brain tissue region is located at a depth below a skin surface that corresponds to the adjustable path length of the reference optical path;
   a sample optical path comprising a lens having a focal depth greater than or equal to the upper bound path length;
   a light source configured to generate reference light to traverse the reference optical path and sample light to traverse the sample optical path;
   a beam combiner configured to form a plurality of interference patterns, respectively corresponding to a plurality of pre-selected phase shifts of the reference light, by merging reference light that has traversed the reference optical path and sample light that has traversed the sample optical path;
   a camera comprising an array of detector pixels, wherein each detector pixel is configured to store a plurality of pixel measurements respectively corresponding to the plurality of interference patterns; and
   a processor in communication with the camera and the light source, wherein the processor is configured to:
      cycle the reference light through the plurality of pre-selected phase shifts in a predetermined time interval by adjusting the reference optical path between the upper bound and the lower bound of the adjustable path length such that the plurality of interference patterns is formed by the beam combiner;
      cause each detector pixel of the array of detector pixels to store the plurality of pixel measurements respectively corresponding to the plurality of interference patterns;
      calculate a pixel value for the each detector pixel based on the stored plurality of pixel measurements of the each detector pixel; and
      calculate a light intensity value representing the activity-dependent optical property of the brain tissue region by averaging the calculated pixel values of the array of detector pixels.

2. The system of claim 1, wherein the lower bound is 5 mm and the upper bound is 50 mm.

3. The system of claim 1, wherein the reference optical path comprises a reference arm and the sample optical path comprises a sample arm.

4. The system of claim 1, wherein the plurality of pre-selected phase shifts comprises two phase shifts in increments of $\pi$.

5. The system of claim 4, wherein the predetermined time interval is from 1 µs to 1 ms.

6. The system of claim 4, wherein each detector pixel comprises two data bins, and the each detector pixel is configured to store the plurality of pixel measurements corresponding to the plurality interference patterns for the two phase shifts by respectively storing the plurality of pixel measurements in the two data bins.

7. The system of claim 6, wherein calculating the pixel value for the each detector pixel comprises calculating an absolute value of a difference of the plurality of pixel measurements of the each detector pixel according to $|B_1[k]-B_2[k]|$ for a kth detector pixel of the detector pixel array, wherein $B_1$ and $B_2$ represent respective values of the plurality of pixel measurements of the each detector pixel.

8. The system of claim 1, wherein the plurality of pre-selected phase shifts comprises four phase shifts in increments of $\pi/2$.

9. The system of claim 8, wherein the predetermined time interval is from 1 μs to 1 ms.

10. The system of claim 8, wherein each detector pixel comprises four data bins, and the each detector pixel is configured to store the plurality of pixel measurements corresponding to the plurality interference patterns for the two phase shifts by respectively storing the plurality of pixel measurements in the four data bins.

11. The system of claim 10, wherein the calculating the pixel value for the each detector pixel comprises calculating a quadrature amplitude of the plurality of pixel measurements of the each detector pixel according to $\text{Sqrt}[(B_2[k]-B_4[k])^2+(B_1[k]-B_3[k])^2]/2$ for a kth detector pixel of the detector pixel array, wherein $B_1$, $B_2$, $B_3$, and $B_4$ represent respective values of the plurality of pixel measurements of the each detector pixel.

12. The system of claim 1, wherein the camera is configured to detect interference pattern changes between the reference light that has traversed the reference optical path and the sample light that has traversed the sample optical path for each of the plurality of pre-selected phase shifts through which the reference light is cycled in the predetermined time interval.

13. The system of claim 1, wherein each detector pixel comprises a plurality of data bins, and the each detector pixel is configured to store the plurality of pixel measurements respectively corresponding to the plurality of interference patterns by respectively storing the plurality of pixel measurements in the plurality of data bins.

14. The system of claim 1, wherein each detector pixel has a width from 1 μm to 1000 μm.

15. The system of claim 1, wherein the predetermined time interval is less than or equal to 1 ms.

16. The system of claim 1, wherein the camera is a lock-in camera.

17. The system of claim 1, wherein the reference optical path comprises a first beam splitter and a mirror, and the sample optical path further comprises a second beam splitter.

18. The system of claim 17, further comprising a first-stage beam splitter that directs the light beam to the first optical path and the second optical path, a first circular polarizing filter disposed in the light beam between the light source and the first-stage beam splitter, and a second circular polarizing filter disposed between the beam combiner and the camera.

19. The system of claim 1, wherein the light source is a low-coherence light source.

20. A non-invasive method for measuring an activity-dependent optical property of a brain tissue region, the method comprising:
  (a) emitting reference light to traverse a reference optical path that defines a reference path length, and emitting sample light to traverse a sample optical path through the brain tissue region, wherein the brain tissue region is located at a depth below a skin surface that corresponds to the reference path length of the reference optical path;
  (b) changing a phase of the reference light according to a set of pre-selected phase shifts within a predetermined time interval;
  (c) combining reference light that has traversed the reference optical path and sample light that has traversed the sample optical path to create a plurality of interference patterns, respectively corresponding to the set of pre-selected phase shifts of the reference light;
  (d) measuring the plurality of interference patterns respectively corresponding to the set of pre-selected phase shifts using a camera comprising an array of detector pixels, wherein each detector pixel stores a plurality of pixel measurements respectively corresponding to the plurality of interference patterns;
  (e) calculating a pixel value for the each detector pixel of the camera based on the stored plurality of pixel measurements of the each detector pixel; and
  (f) calculating a light intensity value representing the activity-dependent optical property of the brain tissue region by averaging the calculated pixel values of the array of detector pixels.

21. The method of claim 20, wherein a number of the pre-selected phase shifts is two, three, or four.

22. The method of claim 21, wherein calculating the pixel value for the each detector pixel comprises a quadrature detection method.

23. The method of claim 21, wherein the pre-selected phase shifts are $\pi/2$, $\pi$, and $3\pi/2$.

24. The method of claim 20, wherein the predetermined time interval is less than a speckle decorrelation time.

25. The method of claim 20, wherein the camera is a lock-in camera, and wherein the each detector pixel comprises a plurality of data bins.

26. The method of claim 25, wherein the each detector pixel stores the plurality of pixel measurements respectively corresponding to the plurality of interference patterns by respectively storing the plurality of pixel measurements in the plurality of data bins.

27. The method of claim 20, wherein the predetermined time interval is less than or equal to 1 ms.

* * * * *